United States Patent
Lin et al.

(10) Patent No.: US 9,504,682 B2
(45) Date of Patent: Nov. 29, 2016

(54) HAPTENS OF ARIPIPRAZOLE

(71) Applicants: JANSSEN PHARMACEUTICA NV, Beerse (BE); Ortho-Clinical Diagnostics, Inc., Raritan, NJ (US)

(72) Inventors: Ronghui Lin, Ambler, PA (US); Rhys Salter, Doylestown, PA (US); Thomas R. DeCory, Pittsford, NY (US); Eric Hryhorenko, Hilton, NY (US); Bart Remmerie, Ghent (BE); Banumathi Sankaran, Pittsford, NY (US)

(73) Assignee: Janssen Pharmaceutica NV, Beerse (BE)

( * ) Notice: Subject to any disclaimer, the term of this patent is extended or adjusted under 35 U.S.C. 154(b) by 92 days.

(21) Appl. No.: 13/970,650

(22) Filed: Aug. 20, 2013

(65) Prior Publication Data

US 2014/0163206 A1    Jun. 12, 2014

Related U.S. Application Data

(60) Provisional application No. 61/691,450, filed on Aug. 21, 2012.

(51) Int. Cl.
| | |
|---|---|
| A61K 31/496 | (2006.01) |
| C07D 401/14 | (2006.01) |
| C07D 401/12 | (2006.01) |
| C07D 215/227 | (2006.01) |
| C07D 215/22 | (2006.01) |
| A61K 47/48 | (2006.01) |

(52) U.S. Cl.
CPC ......... *A61K 31/496* (2013.01); *A61K 47/4833* (2013.01); *A61K 47/48238* (2013.01); *A61K 47/48284* (2013.01); *C07D 215/22* (2013.01); *C07D 215/227* (2013.01); *C07D 401/12* (2013.01); *C07D 401/14* (2013.01)

(58) Field of Classification Search
CPC .............. C07D 401/12; C07D 401/14; A61K 31/496; A61K 47/48284; A61K 47/4833
USPC ........................... 544/363; 530/367, 380, 400
See application file for complete search history.

(56) References Cited

U.S. PATENT DOCUMENTS

| | | | |
|---|---|---|---|
| 4,166,452 | A | 9/1979 | Generales, Jr. |
| 5,527,709 | A | 6/1996 | Danielson et al. |
| 6,034,078 | A | 3/2000 | Fairhurst et al. |
| 8,088,594 | B2 | 1/2012 | Salamone et al. |
| 2006/0046967 | A1 | 3/2006 | Satyam |
| 2006/0251592 | A1 | 11/2006 | Hendler et al. |
| 2010/0069356 | A1 | 3/2010 | Grant et al. |
| 2011/0230520 | A1 | 9/2011 | Sartor et al. |
| 2011/0245224 | A1 | 10/2011 | Barvian et al. |
| 2012/0004165 | A1 | 1/2012 | Keil et al. |
| 2014/0057302 | A1 | 2/2014 | Hryhorenko et al. |
| 2014/0057306 | A1 | 2/2014 | Hryhorenko et al. |

FOREIGN PATENT DOCUMENTS

| | | |
|---|---|---|
| CN | 101821244 | 9/2010 |
| CN | 102260290 A | 11/2011 |
| EP | 0582368 B1 | 1/2001 |
| EP | 0583820 B1 | 3/2002 |
| EP | 2343296 A1 | 7/2011 |
| JP | A-06-94712 | 4/1994 |
| JP | A-H07-247271 | 9/1995 |
| JP | A-2003-516423 | 5/2003 |
| JP | 2006-502698 | 1/2006 |
| JP | 2010-533291 | 10/2010 |
| WO | WO 01/42787 A2 | 6/2001 |
| WO | WO 03/074566 A2 | 9/2003 |
| WO | WO 03/082877 A1 | 10/2003 |
| WO | WO 2004/014895 A1 | 2/2004 |
| WO | WO 2005/028458 A1 | 3/2005 |
| WO | WO 2009/040409 A1 | 4/2009 |
| WO | 2010/151711 | * 12/2010 |
| WO | WO 2010/151711 A1 | 12/2010 |
| WO | WO-2011/012715 A1 | 2/2011 |
| WO | WO2011/022089 A1 | 2/2011 |
| WO | WO-2011/042450 A1 | 4/2011 |
| WO | WO 2011/082076 A1 | 7/2011 |
| WO | WO 2011/112657 A1 | 9/2011 |
| WO | WO 2011/115733 A1 | 9/2011 |
| WO | WO 2011/163594 A2 | 11/2011 |
| WO | 2011/163594 | * 12/2011 |
| WO | WO 2012/012595 A2 | 1/2012 |
| WO | WO-2013/024047 A1 | 2/2013 |
| WO | WO-2013/024048 A1 | 2/2013 |
| WO | WO 2013/088255 A1 | 6/2013 |

OTHER PUBLICATIONS

International Search Report for corresponding Application No. PCT/US2013/055729 dated Oct. 31, 2013.

(Continued)

*Primary Examiner* — James O Wilson
*Assistant Examiner* — Ebenezer O Sackey
(74) *Attorney, Agent, or Firm* — Johnson & Johnson

(57) ABSTRACT

The invention relates to compounds of Formula I, wherein $R^1$, $R^2$, and $R^3$ are defined in the specification, useful for the synthesis of novel conjugates and immunogens derived from aripiprazole. The invention also relates to conjugates of an aripiprazole hapten and a protein.

Formula I

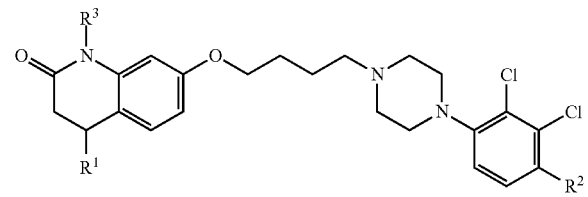

13 Claims, 5 Drawing Sheets

(56) References Cited

OTHER PUBLICATIONS

International Search Report for corresponding Application No. PCT/US2013/055724 dated Sep. 24, 2013.
International Search Report for corresponding Application No. PCT/US2013/055700 dated Oct. 10, 2013.
U.S. Appl. No. 13/971,387, filed Aug. 20, 2013.
U.S. Appl. No. 13/971,416, filed Aug. 20, 2013.
U.S. Appl. No. 13/971,429, filed Aug. 20, 2013.
U.S. Appl. No. 13/971,448, filed Aug. 20, 2013.
U.S. Appl. No. 13/971,475, filed Aug. 20, 2013.
U.S. Appl. No. 13/971,519, filed Aug. 20, 2013.
U.S. Appl. No. 13/971,536, filed Aug. 20, 2013.
U.S. Appl. No. 13/971,546, filed Aug. 20, 2013.
U.S. Appl. No. 13/970,653, filed Aug. 20, 2013.
U.S. Appl. No. 13/970,660, filed Aug. 20, 2013.
U.S. Appl. No. 13/970,667, filed Aug. 20, 2013.
U.S. Appl. No. 13/970,673, filed Aug. 20, 2013.
Abdel-Baki, A., et al., "Pharmacotherapy Challenges in Patients with First-Episode Psychosis", Journal of Affective Disorders, vol. 138, pp. S3-S14 (2012).
Aliouane, L., et al., "Synthesis of Difluoromethylphosphonamidates by Directed Addition of Amine", Tetrahedron Letters, vol. 52, pp. 3681-3685 (2011).
Annuziato, M., et al., "p-Maleimidophenyl Isocyanate: A Novel Heterobifunctional Linker for Hydroxyl to Thiol Coupling", Bioconjugate Chemistry, vol. 4, pp. 212-218 (1993).
Billah, Md., et al. "Directed Immobilization of Reduced Antibody Fragments onto a Novel SAM on Gold for Myoglobin Impedance Immunosensing", Bioelectrochemistry, vol. 80, pp. 49-54 (2010).
Bodin, A., et al., "Identification and Allergenic Activity of Hydroxyaldehydes—A New Type of Oxidation Product from an Ethylated Non-Ionic Surfactant", Contact Dermatitis, vol. 44, pp. 207-212 (2001).
Brinkley, Michael, "A Brief Survey of Methods for Preparing Protein Conjugates with Dyes, Haptens, and Cross-Linking Reagents", Bioconjugate Chemistry, vol. 3, pp. 2-13 (1992).
Chamow, S., et al., "Conjugation of Soluble CD4 without Loss of Biological Activity via a Novel Carbohydrate-Directed Cross-Linking Reagent", The Journal of Biological Chemistry, vol. 267, No. 22, Issue of Aug. 5, pp. 15916-15922 (1992).
Chappey, O., et al., "Monoclonal Antibodies in Hapten Immunossays", Pharmaceutical Research, vol. 9, No. 11, pp. 1375-1379 (1992).
Cleland, W. W., "Dithiothreitol, a New Protective Reagent for SH Groups", Biochemistry, vol. 3, No. 4, pp. 480-482 (1964).
Davis, P., et al., "Development and Validation of an LC-MS/MS Method for the Determination of Quetiapine and Four Related Metabolites in Human Plasma", Journal of Pharmaceutical and Biomedical Analysis, vol. 51, pp. 1113-1119 (2010).
Diago-Meseguer, J., et al., "A New Reagent for Activating Carboxyl Groups, Preparation and Reactions of N,N-Bis[2-oxo-3-oxazolidinyl)phosphorodiamidic Chloride", Syntheses, vol. 7(1), pp. 547-551 (1980).
Danilova, N., et al., "Production and Characterization of Anti-Theophylline Monoclonal Antibodies Suitable for Immunoassay", Immunology Letters, vol. 29, pp. 79-84 (1991).
Fiedler, H., et al., "Surface Chemical Characterization of Maleic Acid Mono[2-4-alkylpiperazinyl)ethyl esters]. 1. The Complex Adsorption Behavior of an Ampholytic Surfactant", Langmuir, vol. 10 pp. 3959-3965 (1994).
Ghetie, V., et al., "Preparation and Characterization of Conjugates of Recombinant CD4 and Deglycosylated Ricin A Chain Using Different Cross-Linkers", Bioconuufate Chemistry, vol. 1, pp. 24-31 (1990).
Gorja, D., et al., "Novel N-Indolylmethyl Substituted Olanzapine Derivatives: Their Design, Synthesis and Evaluation as PDE4B Inhibitors+", Organic & Bimolecular Chemistry, vol. 11, pp. 2075-2079 (2013).

Heykants, J., et al., The Pharmacokinetics of Risperidone in Humans: A Summary, J. Clinical Psychiatry, vol. 55(5), pp. 13-17 (1994).
Huang, M-L, et al., "Pharmacokinetics of the Novel Antipsychotic Agent Risperidone and the Prolactin Response in Healthy Subjects", Clinical Pharmacology Therapeutics, vol. 54, pp. 257-268 (1993).
Kirley, Terence L., Reduction and Fluorescent Labeling of Cystine-Containing Proteins for Subsequent Structural Analyses, Analytical Biochemistry, vol. 180, pp. 231-236 (1989).
Kohler, C., et al., "Continuous Cultures of Fused Cells Secreting Antibody of Predefined Specificity", Nature, vol. 256, Aug. 7, 1975 pp. 495-497.
Konig, W., et al., "A New Method for Synthesizing Peptides: Activation of Carboxyl Molecules With Dicyclohexylcarbodiimide by Adding 1-Hydroxybenzopartriazles", Chem. Ber. vol. 103, pp. 788-798 (1970).
Li, Z., et al., "Synthesis and Characteristization of N-Benzoyl-N'-Carboxyalkyl Substituted Thiourea Derivatives", Phosphorus, Sulfur and Silicon, vol. 178, pp. 293-297 (2003).
Lieberman, J., et al., "Effectiveness of Antipsychotic Drugs in Patients with Chronic Schizophrenia", The New England Journal of Medicine, vol. 353, pp. 1209-1223 (2005).
Liu, H., et al., "Organophosphorus Compound DEPBT as a Coupling Reagent for Oligopeptides and Peptoids Synthesis: Studies on Its Mechanism", Chinese Chemical Letters, vol. 13, No. 7, pp. 601-604 (2002).
Malachowski, W., et al. The Chemistry of Phosphapeptides: Formation of Functionalized Phosphonochloridates Under Mild Conditions and Their Reaction With Alcohols and Amines, Journal of Organic Chemistry, vol. 59, pp. 7616-7624 (1994).
Modena, D., et al, Production and Characterization of Murne Monoclonal Antibodies to Polypeptide Hormones and Their Fragments, Annali Dell'Istitto Superiore di Sanita, vol. 27, No. 1, pp. 167-174 (1991).
Nolli, M., et al., "Antibodies Against the Antibiotics: An Overview", Annali, Istituto Superiore di Sanita, vol. 27, No. 1, pp. 149-154 (1991).
Park, J., et al., "Novel Cyanine Dyes with Vinylsulfone Group for Labeling Biomolecules", Bioconjugate Chemistry, pp. 350-362 (2012).
Penning, T., et al., "Synthesis of Potent Leukotriene $A_4$ Hydrolase Inhibitors. Identification of 3-[Methyl]4-(phenhlmethyl)phenooxy]propyl]amino]propanoic Acid", J. Medical Chemistry, vol. 45, pp. 3482-3490 (2002).
Pruhs, S., et al., "Upscaling the Solid-Phase Synthesis of a Tetrahydrocarabazole in Chemical Development" Organic Process Research & Development, vol. 10, pp. 441-445 (2006).
Van Os, J., et al., "Schizophrenia", Lancet, vol. 374, pp. 635-645 (2009).
Wilbur, D., et al., Reagents for Astatination of Biomolecules; Comparison of the In Vivo Distribution and Stability of Some Radioiodinated/Astatinated Benzamidyl and nido-Carboranyl Compounds, Bioconjugate Chemistry, vol. 15, pp. 203-223 (2004).
Woestenborghs, R., et al, "On the Selectivity of Some Recently Developed RIA's", Methodological Surveys in Biochemistry and Analysis. vol. 20, pp. 241-246 (1990).
Wu, X., et al. "A New Homobifunctional p-Nitro Phenyl Ester XCoupling Reagent for the Preparation of Neoglycoproteins", Organic Letters, vol. 6, No. 24, pp. 4407-4410 (2004).
Gentaur Molecular Products, ID Labs, IDEL-F083 Data Sheet, Enzyme Immunoassay for the Detection of Olanzapine in Urine or Serum, 1-6 (May 2012).
Kubo M., et al., "Development and Validation of an LC-MS/MS method for the quantitative determination of aripiprazole and its main metabolite OPC-14857, in human plasma," Journal of Chromatography B, 2005; 822(1-2):294-299.
Wang Hongyun et al. " LC-MS/MS determination of aripiprazole and dehydroaripiprazole in human plasma," Chinese journal of Pharmaceutical Analysis, vol. 3, Issue 7.

(56) References Cited

OTHER PUBLICATIONS

Japanese Office Action issued in JP 2015-528567, dated Sep. 6, 2016.

Kitagawa, T. et al., "Preparation and Characterization of Hetero-bifunctional Cross-linking Reagents for Protein Modifications," Chem. Pharm. Bull., 1981; 29 (4): 1130-1135.

Rich, D. et al. "Analogues of the Cytostatic Cyclic Tetrapeptide Chlamydocin. Synthesis of Nβ-(N-Maleoylglycyl) and Nβ-(tert-Butyloxycarbonyl) Derivatives of cyclo (Gly-L-Phe-D-Pro-L-Dap)," Journal of Medicinal Chemistry, 1981; 24(5): 567-572.

Holliger, P. et al. "Specific killing of lymphoma cells by cytotoxic T-cells mediated by a bispecific diabody," Protein Engineering, 1996; 9(3): 299-305.

Hermanson, G.T., Bioconjugate Techniques, Zero-Length Cross-Linkers, 1996; 169-186.

Hermanson, G.T., Bioconjugate Techniques, Preparation of Hapten-Carrier Immunogen Conjugates, 1996; 419-455.

* cited by examiner

HAPTENS OF ARIPIPRAZOLE

CROSS REFERENCE TO RELATED APPLICATIONS

This application claims priority of the benefits of the filing of U.S. Provisional Application Ser. No. 61/691,450, filed Aug. 21, 2012. The complete disclosures of the aforementioned related U.S. patent application is/are hereby incorporated herein by reference for all purposes.

FIELD OF THE INVENTION

The invention relates to the field of immunoassays for determining the presence of aripiprazole in human biological fluids.

BACKGROUND OF THE INVENTION

Schizophrenia is a chronic and debilitating psychiatric disorder affecting approximately 0.45-1% of the world's population (van Os, J.; Kapur, S. "Schizophrenia" Lancet 2009, 374, 635-645). The principal goals of treatment are to achieve sustained remission from psychotic symptoms, reduce the risk and consequences of relapse, and improve patient functioning and overall quality of life. While many patients with schizophrenia are able to achieve symptom stability with the available antipsychotic medications, poor adherence to medication is a common reason for relapse with daily administered oral medications. Several studies (Abdel-Baki, A.; Ouellet-Plamondon, C.; Malla, A. "Pharmacotherapy Challenges in Patients with First-Episode Psychosis" Journal of Affective Disorders 2012, 138, S3-S14) investigating the outcomes of non-compliance have shown that patients with schizophrenia who do not take their medication as prescribed have higher rates of relapse, hospital admission and suicide as well as increased mortality. It is estimated that 40 to 75% of patients with schizophrenia have difficulty adhering to a daily oral treatment regimen (Lieberman, J. A.; Stroup, T. S.; McEvoy, J. P.; Swartz, M. S.; Rosenheck, R. A.; Perkins, D. O.; Keefe, R. S. E.; Davis, S. M.; Davis, C. E.; Lebowitz, B. D.; Severe, J.; Hsiao, J. K. "Effectiveness of Antipyschotic Drugs in Patients with Chronic Schizophrenia" New England Journal of Medicine 2005, 353(12), 1209-1223). Therapeutic drug monitoring (TDM) is the quantification of serum or plasma concentrations of drugs, including anti-psychotic drugs, for treatment monitoring and optimization. Such monitoring permits, for example, the identification of patients that are not adhering to their medication regimen, that are not achieving therapeutic doses, that are non-responsive at therapeutic doses, that have suboptimal tolerability, that have pharmacokinetic drug-drug interactions, or that have abnormal metabolism resulting in inappropriate plasma concentrations. Considerable individual variability exists in the patient's ability to absorb, distribute, metabolize, and excrete anti-psychotic drugs. Such differences can be caused by concurrent disease, age, concomitant medication or genetic peculiarities. Different drug formulations can also influence the metabolism of anti-psychotic drugs. TDM permits dose optimization for individual patients, improving therapeutic and functional outcomes. TDM further permits a prescribing clinician to ensure compliance with prescribed dosages and achievement of effective serum concentrations.

To date, methods for determining the levels of serum or plasma concentrations of anti-psychotic drugs involve the use of liquid chromatography (LC) with UV or mass spectrometry detection, and radioimmunoassays (see, for example, Woestenborghs et al., 1990 "On the selectivity of some recently developed RIA's" in Methodological Surveys in Biochemistry and Analysis 20:241-246. Analysis of Drugs and Metabolites, Including Anti-infective Agents; Heykants et al., 1994 "The Pharmacokinetics of Risperidone in Humans: A Summary", J Clin Psychiatry 55/5, suppl:13-17; Huang et al., 1993 "Pharmacokinetics of the novel anti-psychotic agent risperidone and the prolactin response in healthy subjects", Clin Pharmacol Ther 54:257-268). Radioimmunoassays detect one or both of risperidone and paliperidone. Salamone et al. in U.S. Pat. No. 8,088,594 disclose a competitive immunoassay for risperidone using antibodies that detect both risperidone and paliperidone but not pharmacologically inactive metabolites. The antibodies used in the competitive immunoassay are developed against a particular immunogen. ID Labs Inc. (London, Ontario, Canada) markets an ELISA for olanzapine, another antipsychotic drug, which also utilizes a competitive format. The Instructions For Use indicate that the assay is designed for screening purposes and intended for forensic or research use, and is specifically not intended for therapeutic use. The Instructions recommend that all positive samples should be confirmed with gas chromatography/mass spectrometry (GC-MS), and indicate that the antibody used detects olanzapine and clozapine (see ID Labs Inc., "Instructions For Use Data Sheet IDEL-F083", Rev. Date Aug. 8, 2011). Some of these methods, namely HPLC and GC/MS, can be expensive and labor-intensive, and are generally only performed in large or specialty labs having the appropriate equipment.

A need exists for other methods for determining the levels of anti-psychotic drugs, particularly methods that can be performed in a prescribing clinician's office (where the treatment for an individual patient can be adjusted accordingly in a much more timely manner) and in other medical settings lacking LC or GC/MS equipment or requiring rapid test results.

Aripiprazole is:

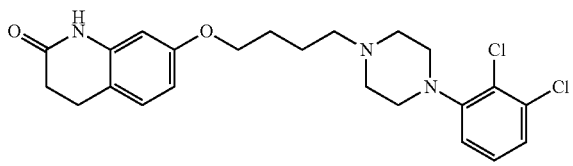 [SMILES: O=C1CCc2ccc(OCCCCN3CCN(c4cccc(Cl)c4Cl)CC3)cc2N1]

SUMMARY OF THE INVENTION

The subject invention provides compounds and conjugates that permit such an improved method for determining the levels of the anti-psychotic drug aripiprazole.

The invention comprises compounds of Formula I:

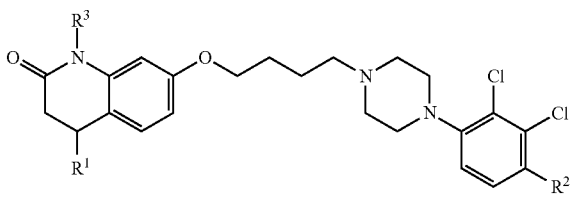

Formula I wherein:
R¹ is H,

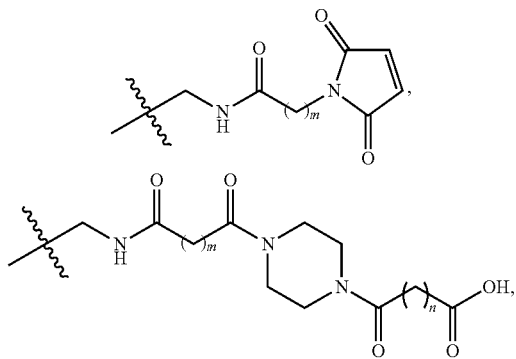

$CH_2NH_2$, $CH_2NHC(O)(CH_2)_mCO_2H$, or $Z-(Y)_p-G$;
R² is H,

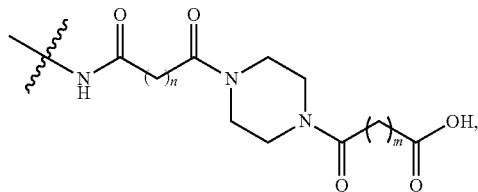

$NH_2$, $NHC(O)(CH_2)_mCO_2H$, or $Z-(Y)_p-G$;
R³ is H, or $W-(Y)_p-G$; provided that two of R¹, R², R³ must be H, and further provided that R¹, R² and R³ may not all be H simultaneously;
wherein:
Z is selected from the group consisting of:
—N(R⁴)—, —O—, —S—, -alkyl-, -alkoxyalkyl-, -aminoalkyl-, -thioalkyl-, -heteroalkyl-, -alkylcarbonyl-,

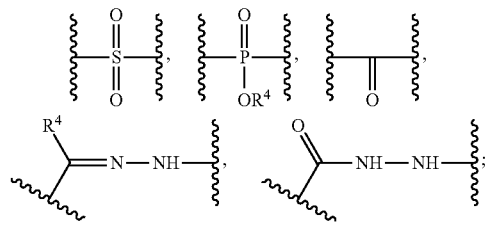

wherein:
W is selected from the group consisting of:
—C(O)—, -alkyl-, -alkoxyalkyl-, -aminoalkyl-, -thioalkyl-, -heteroalkyl-, -alkylcarbonyl-;
R⁴ is H, an alkyl group, cycloalkyl group, aralkyl group or substituted or unsubstituted aryl group;
Y is an organic spacer group;
G is a functional linking group capable of binding to a carrier;
p is 0 or 1;
m is 1, 2, 3, 4, or 5;
n is 1, 2, 3, 4, or 5.

The invention comprises conjugates of compounds of the invention with immunogenic carriers such as proteins, and products produced by the process of contacting the compounds of the invention with immunogenic carriers.

DETAILED DESCRIPTION OF THE INVENTION

Figure 1:
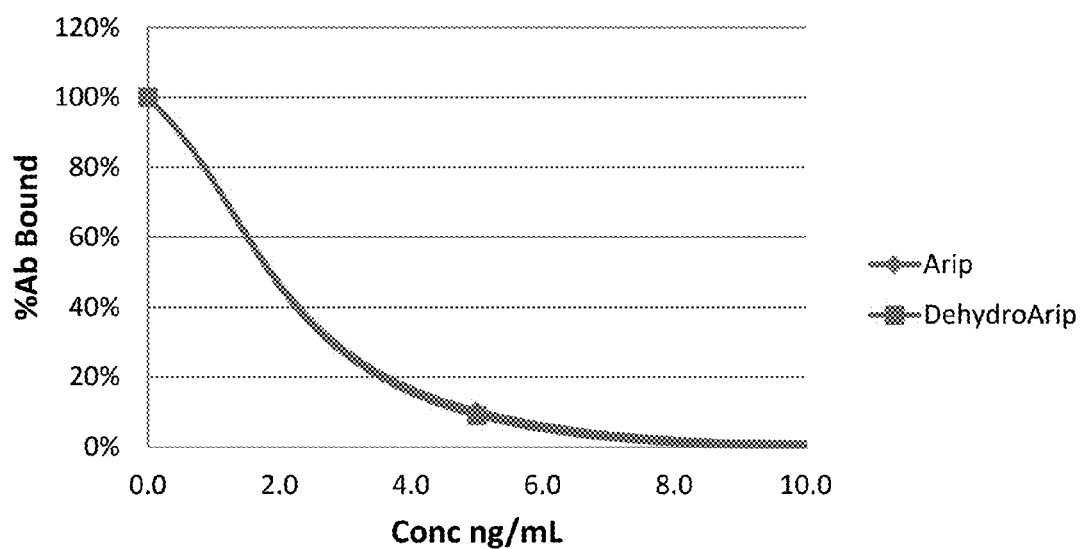
FIG. 1 shows Competition ELISA results generated with hybridoma 3C1.

The subject invention provides compounds and conjugates that permit the determination of levels of anti-psychotic drugs. Such methods will permit clinicians to evaluate objectively at an appointment how likely it is that the worsening of a patient's symptoms may be due to lack of adherence. Alternatively, if compliant, a clinician can consider a different treatment choice. Therapeutic drug monitoring, which is enabled by such methods, is key in identifying the most effective treatment options. Moreover, clinicians believe that such TDM will help them to move into a very different relationship with their patients, i.e., to move from a hypothetical discussion on treatment non-adherence towards a more collaborative one by engaging patients to actively take ownership in optimizing their treatment regimen.

The development of the method requires first the synthesis of several immunogens, comprising a synthetic hapten linked to a protein. A hapten is a small molecule that can elicit an immune response when attached to a large carrier such as a protein. They are protein-free substances, of mostly low molecular weight, which are not capable of stimulating antibody formation alone, but which do react with antibodies. A hapten-protein conjugate is able to stimulate the production of antibodies. Specific antibody generation against small molecules is useful for immunoassay development (*Pharm Res.* 1992, 9(11): 1375-9, *Annali Dell'Istituto Superiore di Sanita.* 1991, 27(1):167-74, *Annali Dell'Istituto Superiore di Sanita.* 1991, 27(1):149-54, *Immunology Letters.* 1991, 28(1):79-83).

The invention comprises compounds of Formula I:

Formula I

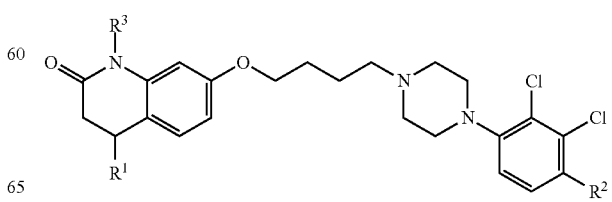

wherein:
R¹ is H,

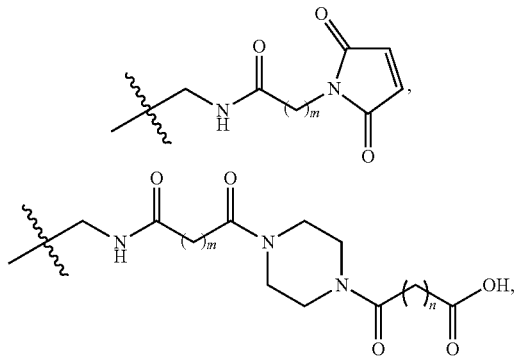

CH$_2$NH$_2$, CH$_2$NHC(O)(CH$_2$)$_m$CO$_2$H, or Z—(Y)$_p$-G;
R² is H,

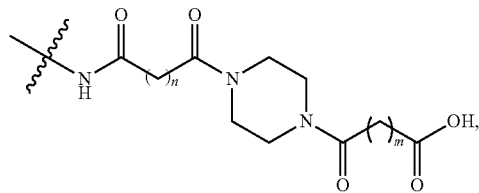

NH$_2$, NHC(O)(CH$_2$)$_m$CO$_2$H, or Z—(Y)$_p$-G;
R³ is H, or W—(Y)$_p$-G; provided that two of R¹, R², R³ must be H, and further provided that R¹, R² and R³ may not all be H simultaneously;
wherein:
Z is selected from the group consisting of:
—N(R⁴)—, —O—, —S—, -alkyl-, -alkoxyalkyl-, -aminoalkyl-, -thioalkyl-, -heteroalkyl-, -alkylcarbonyl-,

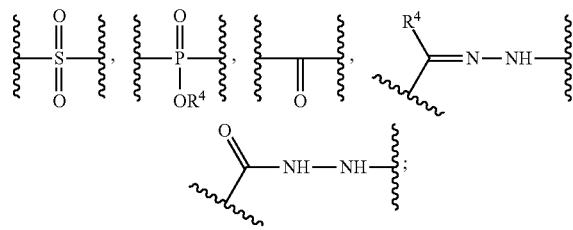

wherein:
W is selected from the group consisting of:
—C(O)—, -alkyl-, -alkoxyalkyl-, -aminoalkyl-, -thioalkyl-, -heteroalkyl-, -alkylcarbonyl-;
R⁴ is H, an alkyl group, cycloalkyl group, aralkyl group or substituted or unsubstituted aryl group;
Y is an organic spacer group;
G is a functional linking group capable of binding to a carrier;
p is 0, or 1;
m is 1, 2, 3, 4, or 5;
n is 1, 2, 3, 4, or 5.

Another embodiment of the invention comprises compounds of Formula I:
wherein:
R¹ is H,

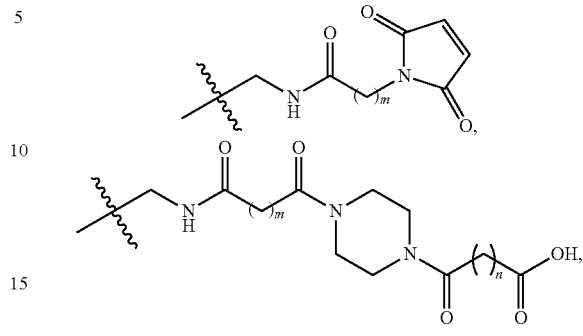

CH$_2$NH$_2$, CH$_2$NHC(O)(CH$_2$)$_m$CO$_2$H, or Z—(Y)$_p$-G;
R² is H,

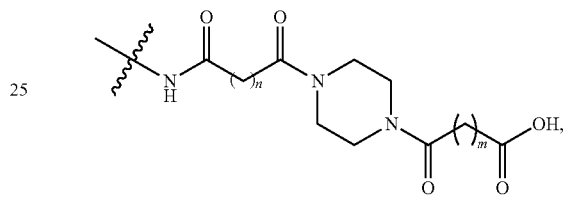

NH$_2$, NHC(O)(CH$_2$)$_m$CO$_2$H, or Z—(Y)$_p$-G;
R³ is H, provided that either R¹ or R² must be H, and further provided that both R¹ and R² may not be H simultaneously;
wherein:
Z is selected from the group consisting of:
—N(R⁴)—, —O—, —S—, -alkyl-, -alkoxyalkyl-, -aminoalkyl-, -thioalkyl-, -heteroalkyl-, -alkylcarbonyl-,

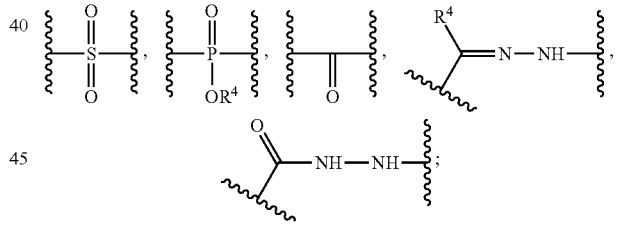

R⁴ is H, an alkyl group, cycloalkyl group, aralkyl group or substituted or unsubstituted aryl group;
Y is an organic spacer group;
G is a functional linking group capable of binding to a carrier;
p is 0, or 1;
m is 1, 2, 3, 4, or 5;
n is 1, 2, 3, 4, or 5.

Another embodiment of the invention comprises compounds of Formula I:
wherein:
R1 is H, or CH$_2$NH—(Y)$_p$-G;
R2 is H, or NH—(Y)$_p$-G;
R³ is H, provided that either R¹ or R² must be H, and further provided that both R¹ and R² may not be H simultaneously;
wherein:
Y is an organic spacer group;
G is a functional linking group capable of binding to a carrier;
p is 1.

Another embodiment of the invention comprises compounds of Formula I:
wherein:
$R^1$ is H,

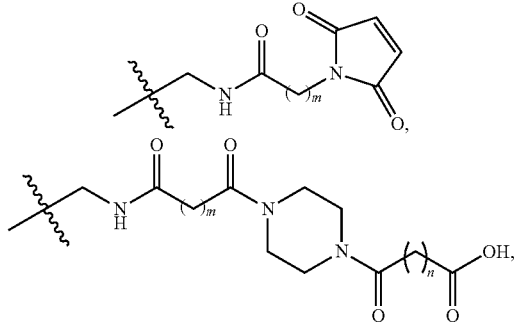

$CH_2NH_2$, or $CH_2NHC(O)(CH_2)_mCO_2H$;
$R^2$ is H,

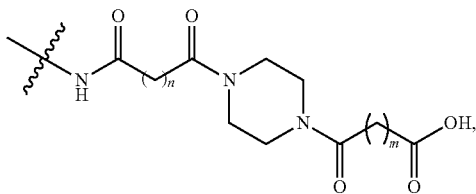

$NH_2$, or $NHC(O)(CH_2)_nCO_2H$; provided that either $R^1$ or $R^2$ must be H, and further provided that both $R^1$ and $R^2$ may not be H simultaneously;

$R^3$ is H;

m is 1, 2, 3, 4, or 5;

n is 1, 2, 3, 4, or 5.

In another embodiment of the invention:

$R^1$ is H, $CH_2NH_2$, or $CH_2NHC(O)(CH_2)_mCO_2H$; $R^2$ is H, $NH_2$, or $NHC(O)(CH_2)_nCO_2H$;

provided that either $R^1$ or $R^2$ must be H, and further provided that both $R^1$ and $R^2$ may not be H simultaneously;

$R^3$ is H;

m is 1, 2 or 3;

n is 1, 2 or 3.

In another embodiment of the invention:

$R^1$ is H, $CH_2NH_2$, or $CH_2NHC(O)(CH_2)_mCO_2H$;

$R^2$ is H, $NH_2$, or $NHC(O)(CH_2)_nCO_2H$; provided that either $R^1$ or $R^2$ must be H, and further provided that both $R^1$ and $R^2$ may not be H simultaneously;

$R^3$ is H;

m is 2;

n is 2.

Another embodiment of the invention is a compound selected from the group consisting of:

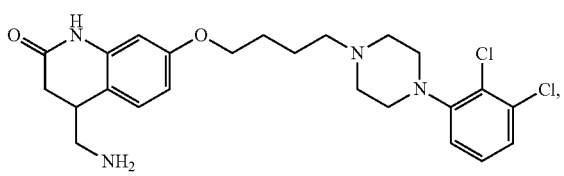 [SMILES: NCC1CC(=O)Nc2cc(OCCCCN3CCN(c4cccc(Cl)c4Cl)CC3)ccc21]

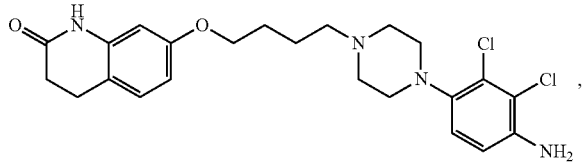

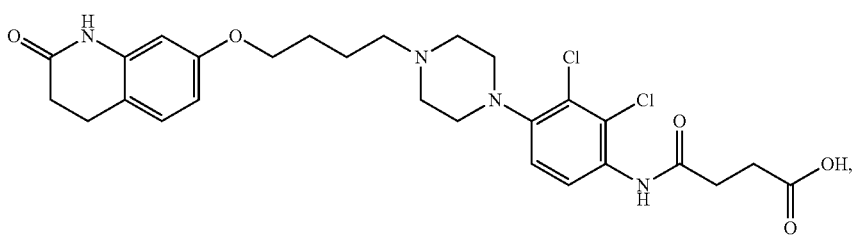

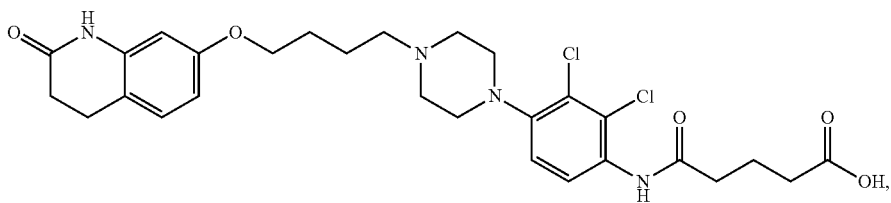

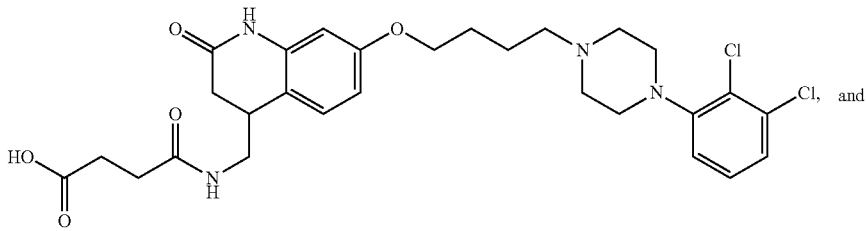

-continued

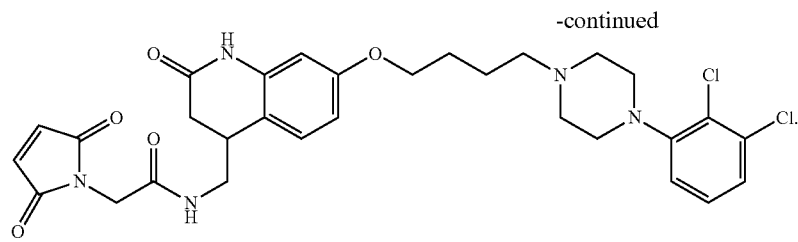

A preferred embodiment of the invention is the compound:

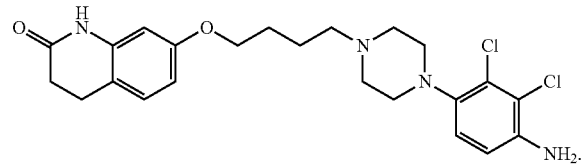 [SMILES: Nc1ccc(N2CCN(CCCCOc3ccc4c(c3)NC(=O)CC4)CC2)c(Cl)c1Cl]

Another preferred embodiment of the invention is the compound:

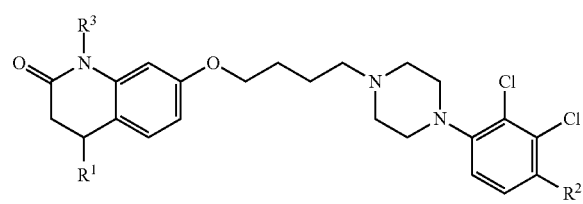

The invention further provides conjugates of the above compounds with an immunogenic carrier.

Another embodiment of the invention is thus a conjugate of the compound of Formula I Formula I

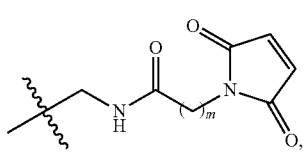

wherein:
$R^1$ is H,

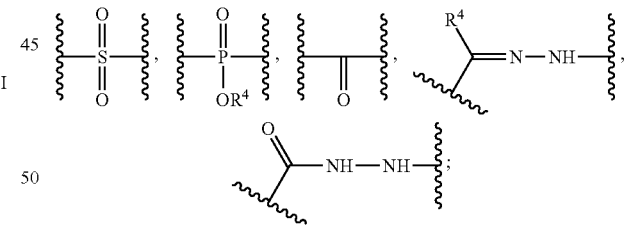

-continued

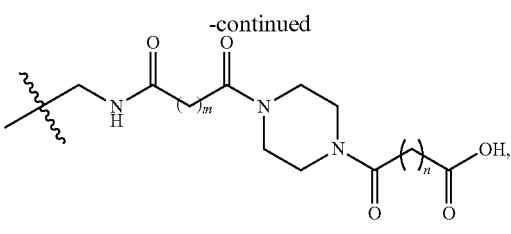

$CH_2NH_2$, $CH_2NHC(O)(CH_2)_mCO_2H$, or $Z-(Y)_p$-G;
$R^2$ is H, $NH_2$, $NHC(O)(CH_2)_mCO_2H$, or $Z-(Y)_p$-G;
$R^3$ is H, or $W-(Y)_p$-G; provided that two of $R^1$, $R^2$, $R^3$ must be H, and further provided that $R^1$, $R^2$ and $R^3$ may not all be H simultaneously;
wherein:
Z is selected from the group consisting of:
—$NR^4$—, —O—, —S—, -alkyl-, -alkoxyalkyl-, -aminoalkyl-, -thioalkyl-, -heteroalkyl-, alkylcarbonyl-, —$R^4$ is H, an alkyl group, cycloalkyl group or substituted or unsubstituted aryl group;
wherein:
W is selected from the group consisting of:
—C(O)—, -alkyl-, -alkoxyalkyl-, -aminoalkyl-, -thioalkyl-, -heteroalkyl-, -alkylcarbonyl-;
Y is an organic spacer group;
G is a functional linking group capable of binding to a carrier;
p is 0, or 1;
m is 1, 2, 3, 4, or 5;
n is 1, 2, 3, 4, or 5; and an immunogenic carrier.

Another embodiment of the invention is a conjugate of the compound of Formula I wherein:
$R^1$ is H,

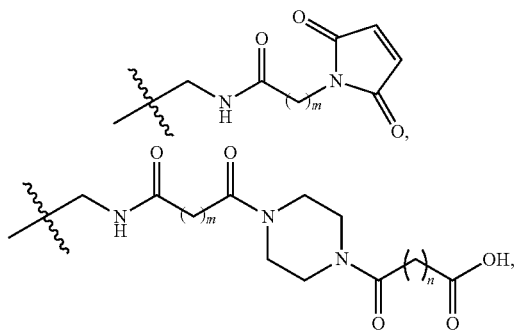

$CH_2NH_2$, $CH_2NHC(O)(CH_2)_mCO_2H$, or $Z—(Y)_p$-G;
$R^2$ is H,

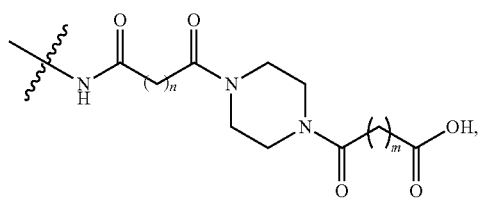

$NH_2$, $NHC(O)(CH_2)_mCO_2H$, or $Z—(Y)_p$-G;
provided that either $R^1$ or $R^2$ must be H, and further provided that both $R^1$ and $R^2$ may not be H simultaneously;
$R^3$ is H;
wherein:
Z is selected from the group consisting of:
—$NR^4$—, —O—, —S—, -alkyl-, -alkoxyalkyl-, -aminoalkyl-, -thioalkyl-, -heteroalkyl-, -alkylcarbonyl-,

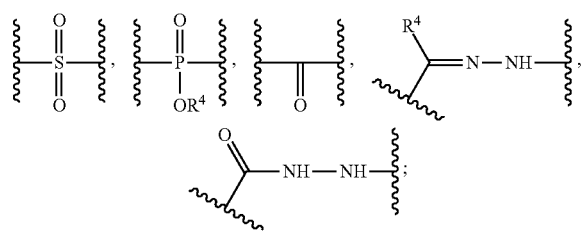

$R^4$ is H, an alkyl group, cycloalkyl group or substituted or unsubstituted aryl group;
Y is an organic spacer group;
G is a functional linking group capable of binding to a carrier;
p is 0 or 1;
m is 1, 2, 3, 4, or 5;
n is 1, 2, 3, 4, or 5; and an immunogenic carrier.
Another embodiment of the invention is a conjugate of the compound of Formula I wherein:
$R^1$ is H, or $CH_2NH—(Y)_p$-G;
$R^2$ is H, or $NH—(Y)_p$-G;
$R^3$ is H, provided that either $R^1$ or $R^2$ must be H, and further provided that both $R^1$ and $R^2$ may not be H simultaneously;

wherein:
Y is an organic spacer group;
G is a functional linking group capable of binding to a carrier;
p is 1; and an immunogenic carrier.
Another embodiment of the invention is a conjugate of the compound of Formula I
wherein:
$R^1$ is H,

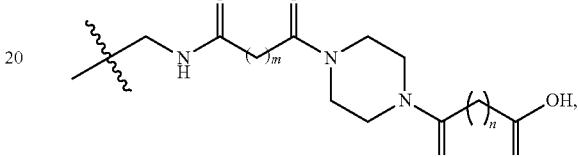

$CH_2NH_2$, $CH_2NHC(O)(CH_2)_mCO_2H$;
$R^2$ is H,

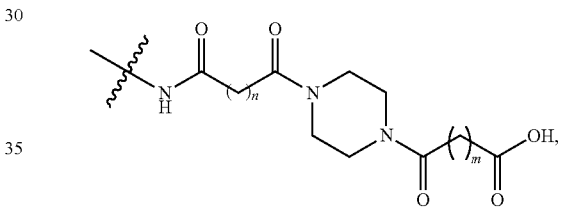

$NH_2$, $NHC(O)(CH_2)_mCO_2H$;
provided that either $R^1$ or $R^2$ must be H, and further provided that both $R^1$ and $R^2$ may not be H simultaneously;
$R^3$ is H;
m is 1, 2, 3, 4, or 5;
n is 1, 2, 3, 4, or 5; and an immunogenic carrier.
Another embodiment of the invention is a conjugate of the compound of Formula I
wherein:
$R^1$ is H, $CH_2NH_2$, or $CH_2NHC(O)(CH_2)_mCO_2H$;
$R^2$ is H, $NH_2$, or $NHC(O)(CH_2)_nCO_2H$; provided that either $R^1$ or $R^2$ must be H, and further provided that both $R^1$ and $R^2$ may not be H simultaneously;
m is 1, 2 or 3;
n is 1, 2 or 3; and an immunogenic carrier.
Another embodiment of the invention is a conjugate of the compound of Formula I
wherein:
$R^1$ is H, $CH_2NH_2$, or $CH_2NHC(O)(CH_2)_mCO_2H$;
$R^2$ is H, $NH_2$, or $NHC(O)(CH_2)_nCO_2H$; provided that either $R^1$ or $R^2$ must be H, and further provided that both $R^1$ and $R^2$ may not be H simultaneously;
m is 2;
n is 2; and an immunogenic carrier.
Another embodiment of the invention is a conjugate of a compound selected from the group consisting of:

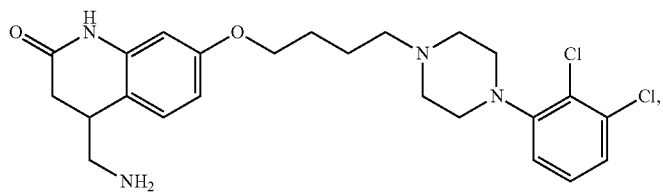

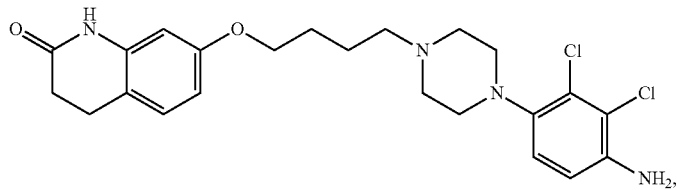

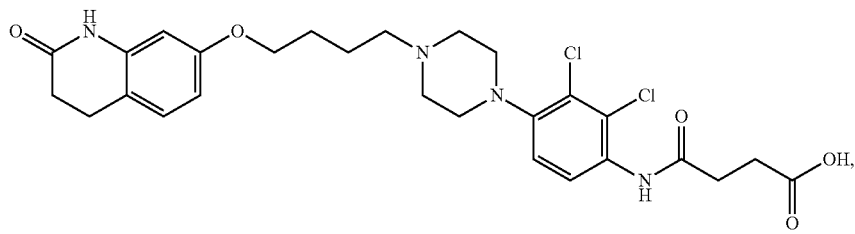

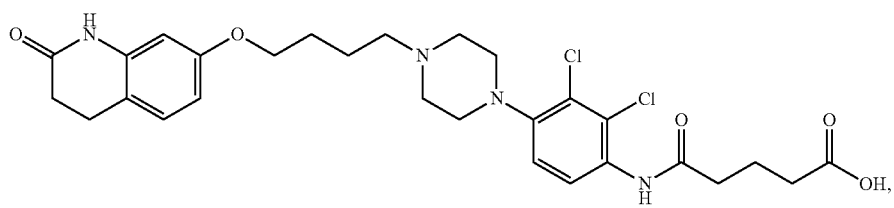

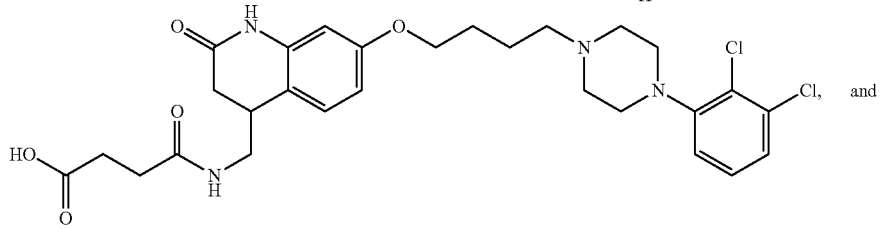

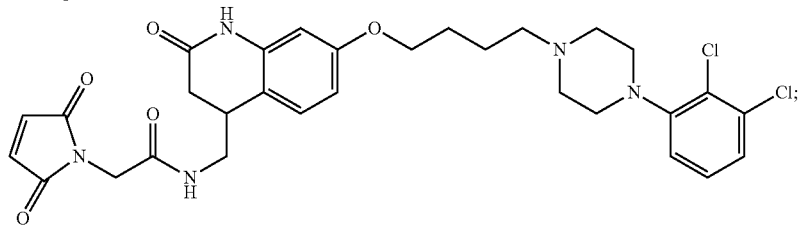

and an immunogenic carrier.

A preferred embodiment of the invention is any of the above conjugates wherein the immunogenic carrier is a protein.

A preferred embodiment of the invention is any of the above conjugates, wherein said protein is keyhole limpet hemocyanin, ovalbumin or bovine thyroglobulin.

The invention also provides products formed from the process of contacting the above compounds with an immunogenic carrier.

Another embodiment of the invention is thus a product formed from the process of contacting a compound of Formula I

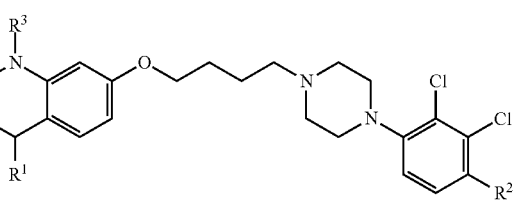

Formula I wherein:
R¹ is H,

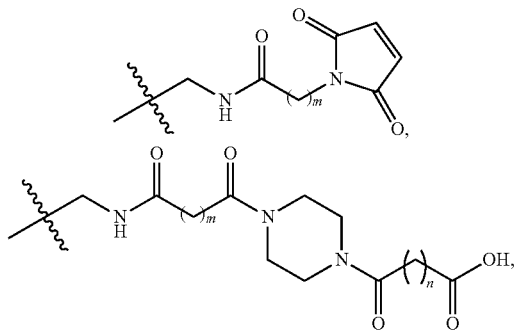

$CH_2NH_2$, $CH_2NHC(O)(CH_2)_mCO_2H$, or Z—(Y)$_p$-G;
R² is H,

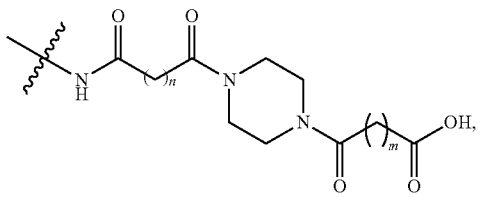

$NH_2$, $NHC(O)(CH_2)_mCO_2H$, or Z—(Y)$_p$-G;
R³ is H, or W—(Y)$_p$-G; provided that two of R¹, R², R³ must be H, and further provided that R¹, R² and R³ may not all be H simultaneously;
wherein:
Z is selected from the group consisting of:
—NR⁴—, —O—, —S—, -alkyl-, -alkoxyalkyl-, -aminoalkyl-, -thioalkyl-, -heteroalkyl-, alkylcarbonyl-,

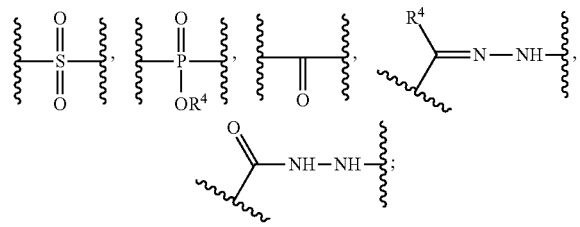

—R⁴ is H, an alkyl group, cycloalkyl group or substituted or unsubstituted aryl group;
wherein:
W is selected from the group consisting of:
—C(O)—, -alkyl-, -alkoxyalkyl-, -aminoalkyl-, -thioalkyl-, -heteroalkyl-, -alkylcarbonyl-;
Y is an organic spacer group;
G is a functional linking group capable of binding to a carrier;
p is 0, or 1;
m is 1, 2, 3, 4, or 5;
n is 1, 2, 3, 4, or 5; with an immunogenic carrier.

Another embodiment of the invention is a product formed from the process of contacting a compound of Formula I wherein:
R¹ is H,

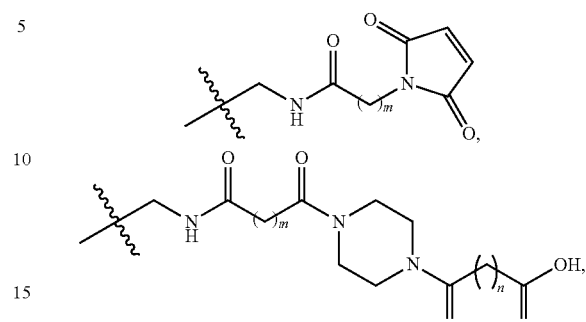

$CH_2NH_2$, $CH_2NHC(O)(CH_2)_mCO_2H$, or Z—(Y)$_p$-G;
R² is H,

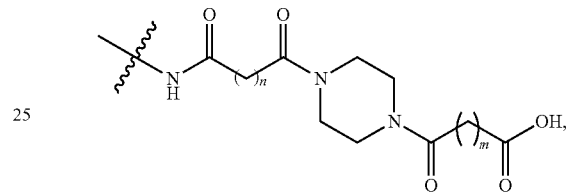

$NH_2$, $NHC(O)(CH_2)_mCO_2H$, or Z—(Y)$_p$-G;
provided that either R¹ or R² must be H, and further provided that both R¹ and R² may not be H simultaneously;
R³ is H;
wherein:
Z is selected from the group consisting of:
—NR⁴—, —O—, —S—, -alkyl-, -alkoxyalkyl-, -aminoalkyl-, -thioalkyl-, -heteroalkyl-, -alkylcarbonyl-,

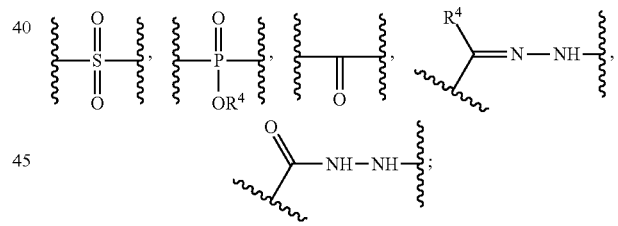

R⁴ is H, an alkyl group, cycloalkyl group or substituted or unsubstituted aryl group;
Y is an organic spacer group;
G is a functional linking group capable of binding to a carrier;
p is 0, or 1;
m is 1, 2, 3, 4, or 5;
n is 1, 2, 3, 4, or 5; with an immunogenic carrier.

Another embodiment of the invention is a product formed from the process of contacting a compound of Formula I
wherein:
R¹ is H, or $CH_2NH$—(Y)$_p$-G;
R² is H, or NH—(Y)$_p$-G;
R³ is H, provided that either R¹ or R² must be H, and further provided that both R¹ and R² may not be H simultaneously;
wherein:
Y is an organic spacer group;
G is a functional linking group capable of binding to a carrier;

p is 1; with an immunogenic carrier.

Another embodiment of the invention is a product formed from the process of contacting a compound of Formula I wherein:

$R^1$ is H,

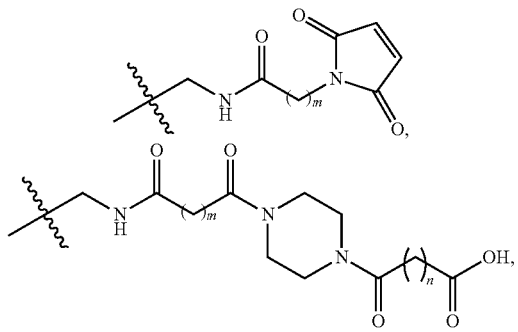

$CH_2NH_2$, $CH_2NHC(O)(CH_2)_mCO_2H$;
$R^2$ is H,

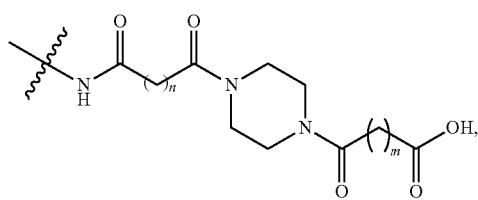

$NH_2$, $NHC(O)(CH_2)_mCO_2H$;

provided that either $R^1$ or $R^2$ must be H, and further provided that both $R^1$ and $R^2$ may not be H simultaneously;
$R^3$ is H;
m is 1, 2, 3, 4, or 5;
n is 1, 2, 3, 4, or 5; with an immunogenic carrier.

Another embodiment of the invention is a product formed from the process of contacting a compound of Formula I wherein:

$R^1$ is H, $CH_2NH_2$, or $CH_2NHC(O)(CH_2)_mCO_2H$;

$R^2$ is H, $NH_2$, or $NHC(O)(CH_2)_nCO_2H$; provided that either $R^1$ or $R^2$ must be H, and further provided that both $R^1$ and $R^2$ may not be H simultaneously;

m is 1, 2 or 3;

n is 1, 2 or 3; with an immunogenic carrier.

Another embodiment of the invention is a product formed from the process of contacting a compound of Formula I wherein:

$R^1$ is H, $CH_2NH_2$, or $CH_2NHC(O)(CH_2)_mCO_2H$;

$R^2$ is H, $NH_2$, or $NHC(O)(CH_2)_nCO_2H$; provided that either $R^1$ or $R^2$ must be H, and further provided that both $R^1$ and $R^2$ may not be H simultaneously;

m is 2;

n is 2; with an immunogenic carrier.

A preferred embodiment of the invention is a product formed from the process of contacting the compound

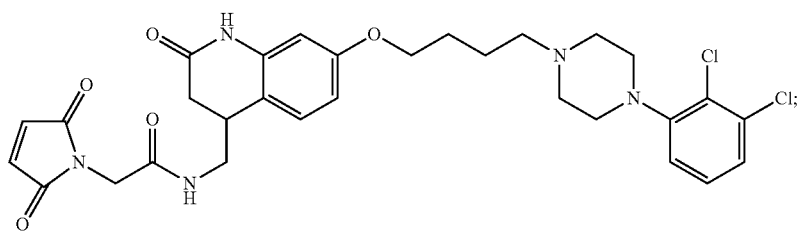 [SMILES: O=C(CN1C(=O)C=CC1=O)NCC1CC(=O)Nc2cc(OCCCCN3CCN(c4cccc(Cl)c4Cl)CC3)ccc21]

with an immunogenic carrier.

A preferred embodiment of the invention is a product formed from the process of contacting the compound

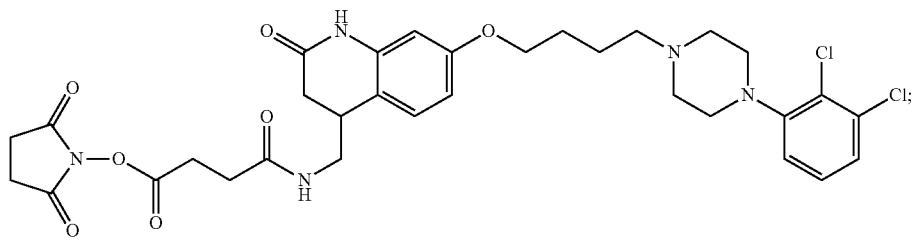 [SMILES: O=C(CCC(=O)ON1C(=O)CCC1=O)NCC1CC(=O)Nc2cc(OCCCCN3CCN(c4cccc(Cl)c4Cl)CC3)ccc21]

with an immunogenic carrier.

A preferred embodiment of the invention is a product formed from the process of contacting the compound

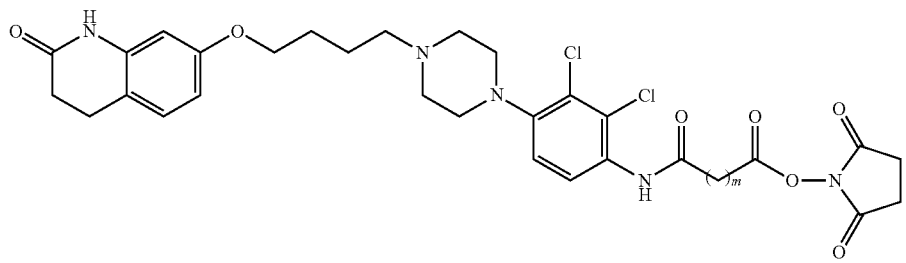

wherein m is 2 or 3; with an immunogenic carrier.

A preferred embodiment of the invention is any of the above products wherein the immunogenic carrier is a protein.

A preferred embodiment of the invention is any of the above products, wherein said protein is keyhole limpet hemocyanin, ovalbumin or bovine thyroglobulin.

ABBREVIATIONS

Herein and throughout the application, the following abbreviations may be used.
AIBN azobisisobutyronitrile
AMAS N-(α-maleimidoacetoxy)succinimide ester
BTG bovine thyroglobulin
$Bu_3N$ tributylamine
DMF N,N-dimethylformamide
EDTA ethylenediaminetetraaceticacid
EtOH ethyl alcohol
KLH keyhole limpet hemocyanin
NBS N-bromo succinimide
SATA N-succinimidyl S-acetylthioacetate
THF tetrahydrofuran
TFA trifluoroacetic acid
DCC dicyclohexylcarbodiimide
DIC diisopropylcarbodiimide
DMAP N,N-dimethyl-4-aminopyridine
EDC 1-ethyl-3(3-dimethylaminopropyl) carbodiimidehydrochloride
NHS N-hydroxysuccinimide
TFP Tetrafluorophenyl
PNP p-nitrophenyl
TBTU O-(Benzotriazol-1-yl)-N,N,N',N'-tetramethyluronium tetrafluoroborate
HOBT N-Hydroxybenzotriazole
DEPBT 3-(diethoxyphosphoryloxy)-1,2,3-benzotrazin-4(3H)-one
BOP-Cl Bis(2-oxo-3-oxazolidinyl)phosphonic chloride
DTT dithioerythritol

DEFINITIONS

The term "conjugate" refers to any substance formed from the joining together of separate parts. Representative conjugates in accordance with the present invention include those formed by the joining together of a small molecule, such as the compounds of Formula I, and a large molecule, such as a carrier or a polyamine polymer, particularly a protein. In the conjugate the small molecule may be joined at one or more active sites on the large molecule.

The term "hapten" refers to a partial or incomplete antigen. A hapten is a protein-free substance, which is not capable of stimulating antibody formation, but which does react with antibodies. The antibodies are formed by coupling a hapten to a high molecular weight immunogenic carrier, and then injecting this coupled product, i.e., an immunogen, into a human or animal subject.

The term "immunogen" refers to a substance capable of eliciting, producing, or generating an immune response in an organism.

An "immunogenic carrier," as used herein, is an immunogenic substance, commonly a protein, that can join at one or more positions with haptens, thereby enabling the production of antibodies that can bind specifically with these haptens. Examples of immunogenic carrier substances include, but are not limited to, proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Various protein types may be employed as immunogenic carriers, including without limitation, albumins, serum proteins, lipoproteins, etc. Illustrative proteins include bovine serum albumin, keyhole limpet hemocyanin, egg ovalbumin, bovine thyroglobulin, fraction V human serum albumin, rabbit albumin, pumpkin seed globulin, diphtheria toxoid, tetanus toxoid, botilinus toxin, succinylated proteins, and synthetic poly(aminoacids) such as polylysine.

Immunogenic carriers can also include poly amino-polysaccharides, which are a high molecular weight polymers built up by repeated condensations of monosaccharides. Examples of polysaccharides are starches, glycogen, cellulose, carbohydrate gums such as gum arabic, agar, and so forth. The polysaccharide also contains poly(amino acid) residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

The term "derivative" refers to a chemical compound or molecule made from a parent compound by one or more chemical reactions.

The term "analogue" of a chemical compound refers to a chemical compound that contains a chain of carbon atoms and the same particular functional groups as a reference compound, but the carbon chain of the analogue is longer or shorter than that of the reference compound.

A "label," "detector molecule," "reporter" or "detectable marker" is any molecule which produces, or can be induced to produce, a detectable signal. The label can be conjugated to an analyte, immunogen, antibody, or to another molecule such as a receptor or a molecule that can bind to a receptor such as a ligand, particularly a hapten or antibody. Non-limiting examples of labels include radioactive isotopes (e.g., $^{125}$I), enzymes (e.g., β-galactosidase, peroxidase), enzyme fragments, enzyme substrates, enzyme inhibitors, coenzymes, catalysts, fluorophores (e.g., rhodamine, fluorescein isothiocyanate or FITC, or Dylight 649), dyes, chemiluminescers and luminescers (e.g., dioxetanes, luciferin), or sensitizers.

As used herein, a "spacer" refers to a portion of a chemical structure which connects two or more substructures such as haptens, carriers, immunogens, labels or binding partners through a functional linking group. These spacer groups are composed of the atoms typically present and assembled in ways typically found in organic compounds and so may be referred to as "organic spacing groups". The chemical building blocks used to assemble the spacers will be described hereinafter in this application. Among the preferred spacers are straight or branched, saturated or unsaturated carbon chains. These carbon chains may also include one or more heteroatoms within the chain, one or more heteroatoms replacing one or more hydrogens of any carbon atom in the chain, or at the termini of the chains. By "heteroatoms" is meant atoms other than carbon which are chosen from the group consisting of oxygen, nitrogen, phosphorous and sulfur, wherein the nitrogen, phosphorous and sulfur atoms may exist in any oxidation state and may have carbon or other heteroatoms bonded to them. The spacer may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. Preferred chain lengths are between 1 to 20 atoms.

A "functional linking group" refers to a reactive group that is present on a hapten and may be used to provide an available reactive site through which the hapten portion may be coupled to another moiety through formation of a covalent chemical bond to produce a conjugate of a hapten with another moiety (such as a label or carrier). The hapten may be linked in this way to a moiety such as biotin to form a competitive binding partner for the hapten.

Spacer groups may be used to link the hapten to the carrier. Spacers of different lengths allow one to attach the hapten with differing distances from the carrier for presentation to the immune system of the animal or human being immunized for optimization of the antibody formation process. Attachment to different positions in the hapten molecule allows the opportunity to present specific sites on the hapten to the immune system to influence antibody recognition. The spacer may contain hydrophilic solubilizing groups to make the hapten derivative more soluble in aqueous media. Examples of hydrophilic solubilizing groups include but are not limited to polyoxyalkyloxy groups, for example, polyethylene glycol chains; hydroxyl, carboxylate and sulfonate groups.

The term "nucleophilic group" or "nucleophile" refers to a species that donates an electron-pair to form a chemical bond in a reaction. The term "electrophilic group" or "electrophile" refers to a species that accepts an electron-pair from a nucleophile to form a chemical bond in a reaction.

The term "substituted" refers to substitution of an atom or group of atoms in place of a hydrogen atom on a carbon atom in any position on the parent molecule. Non limiting examples of substituents include halogen atoms, amino, hydroxy, carboxy, alkyl, aryl, heteroalkyl, heteroaryl, cyano, alkoxy, nitro, aldehyde and ketone groups.

The term "alkyl" refers to saturated or unsaturated linear and branched chain radicals of up to 12 carbon atoms, unless otherwise indicated, and is specifically intended to include radicals having any degree or level of saturation. Alkyl includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated monocyclic or bicyclic hydrocarbon ring radical composed of from 3 to 10 carbon atoms. Alkyl substituents may optionally be present on the ring. Examples include cyclopropyl, 1,1-dimethyl cyclobutyl, 1,2,3-trimethylcyclopentyl, cyclohexyl and cyclohexenyl.

The term "heteroatom" refers to a nitrogen atom, an oxygen atom, a phosphorous atom or a sulfur atom wherein the nitrogen, phosphorous and sulfur atoms can exist in any allowed oxidation states.

The term "heteroalkyl" refers to an alkyl group that includes one or more heteroatoms within the chain, one or more heteroatoms replacing one or more hydrogens of any carbon atom in the chain, or at termini of the chains.

The term "heterocyclyl" refers to a nonaromatic (i.e. saturated or partially unsaturated) ring composed of from 3 to 7 carbon atoms and at least one heteroatom selected from N, O or S. Alkyl substituents may optionally be present on the ring. Examples include tetrahydrofuryl, dihydropyranyl, piperidyl, 2,5-dimethypiperidyl, morpholinyl, piperazinyl, thiomorpholinyl, pyrrolidinyl, pyrrolinyl, pyrazolidinyl, pyrazolinyl, imidazolidinyl and imidazolinyl.

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain.

The term "alkoxy" refers to straight or branched chain radicals of up to 12 carbon atoms, unless otherwise indicated, bonded to an oxygen atom. Examples include but are not limited to methoxy, ethoxy, propoxy, isopropoxy and butoxy.

The term "alkoxyalkyl" refers to at least one alkoxy group bonded to any carbon atom along an alkyl chain.

The term "polyalkoxyalkyl" refers to long-chain alkoxy compounds and includes polyethylene glycols of discreet or monodispersed sizes.

The term "thioalkyl" refers to at least one sulfur group bonded to any carbon atom along an alkyl chain. The sulfur group may be at any oxidation state and includes sulfoxides, sulfones and sulfates.

The term "carboxyalkyl" refers to at least one carboxylate group bonded to any carbon atom along an alkyl chain. The term "carboxylate group" includes carboxylic acids and alkyl, cycloalkyl, aryl or aralkyl carboxylate esters.

The term "alkylcarbonyl" refers to a group that has a carbonyl group bonded to any carbon atom along an alkyl chain.

The term "heteroaryl" refers to 5- to 7-membered mono- or 8- to 10-membered bicyclic aromatic ring radicals, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "aryl" refers to monocyclic or bicyclic aromatic ring radicals containing from 6 to 12 carbons in the ring. Alkyl substituents may optionally be present on the ring. Examples include phenyl, biphenyl and napththalene.

The term "aralkyl" refers to a $C_{1-6}$ alkyl group containing an aryl substituent. Examples include benzyl, phenylethyl or 2-naphthylmethyl.

The term "acyl" refers to the group —C(O)$R_a$, where $R_a$ is hydrogen, alkyl, cycloalkyl, heteroalkyl, aryl, aralkyl and heteroaryl. An "acylating agent" adds the —C(O)$R_a$ group to a molecule.

The term "sulfonyl" refers to the group —S(O)$_2R_b$, where $R_b$ is hydrogen, alkyl, cycloalkyl, heteroalkyl, haloalkyl, aryl, aralkyl and heteroaryl. A "sulfonylating agent" adds the —S(O)$_2R_a$ group to a molecule.

Spacers bearing reactive functional linking groups for the attachment of haptens to carrier moieties may be prepared by a wide variety of methods. The spacer may be formed using a molecule that is differentially functionalized or activated with groups at either end to allow selective sequential reaction with the hapten and the carrier, but the same reactive moiety may also be used at both ends. The groups selected for reaction with the hapten and the functional linking group to be bound to the carrier are determined by the type of functionality on the hapten and the carrier that the hapten is to be bonded with. Spacers and methods of attachment to haptens and carriers include but are not limited to those described by Brinkley, M., A., *Bioconjugate Chem.* 1992, 3:2-13, Hermanson, Greg T., *Bioconjugate Techniques*, Academic Press, London, Amsterdam, Burlington, Mass., USA, 2008 and *Thermo Scientific Pierce Crosslinking Technical Handbook*; available for download or hard copy request from Thermo Scientific 3747 N Meridian Rd, Rockford, Ill. USA 61101, ph 800-874-3723 or at: http://www.piercenet.com/and references within. Many differentially activated molecules for formation of spacer groups are commercially available from vendors, for example Thermo Scientific.

For haptens bearing an amino group, modes of attachment of the spacer to the hapten include reaction of the amine on the hapten with a spacer building block bearing an acyl halide or active ester. "Active esters" are defined as esters that undergo reaction with a nucleophilic group, for example an amino group, under mild conditions to form a stable linkage. A stable linkage is defined as one that remains intact under conditions of further use, for example subsequent synthetic steps, use as an immunogen, or in a biochemical assay. A preferred example of a stable linkage is an amide bond. Active esters and methods of formation are described by Benoiton, N. L., in Houben-Weyl, *Methods of Organic Chemistry*, Thieme Stuttgart, N.Y., vol E22 section 3.2:443 and Benoiton, N. L., *Chemistry of Peptide Synthesis*, Taylor and Francis, N Y, 2006. Preferred active esters include p-nitrophenyl ester (PNP), N-hydroxysuccinimide ester (NHS) and tetrafluorophenyl ester (TFP). Acyl halides may be prepared by many methods known to one skilled in the art for example, reaction of the carboxylic acid with thionyl chloride or oxalyl chloride, see: Fieser, L. F. and Fieser, M. *Reagents for Organic Synthesis*, John Wiley and Sons, NY, 1967 and references within. These may be converted to other active esters such as p-nitrophenyl esters (PNP) which may also be used in active bi-functional spacers as described by Wu et. al, *Organic Letters*, 2004, 6 (24):4407. N-hydroxysuccinimide (NHS) esters may be prepared by reaction of N,N-disuccinimidyl carbonate (CAS 74124-79-1) with the carboxylic acid of a compound in the presence of an organic base such as triethylamine or diisopropylethylamine in an aprotic solvent under anhydrous conditions as described in example 35 of WO2012012595 or by using N-hydroxysuccinimide and dicyclohexylcarbodiimide (DCC) or other dehydrating agent, under anhydrous conditions. Tetrafluorophenyl esters (TFP) may be prepared by reaction of carboxylic acids with 2,3,5,6-tetrafluorophenyltrifluoroacetate in the presence of an organic base such as triethylamine or diisopropylethylamine in an aprotic solvent under anhydrous conditions as reported by Wilbur, et. al, *Bioconjugate Chem.*, 2004, 15(1):203. One skilled in the art will recognize that spacers shown in Table 1, among others, can be obtained using known methods and attached to amino-bearing haptens utilizing routine optimization of reaction conditions. These spacers allow attachment of the hapten to a thiol group on a carrier.

TABLE 1

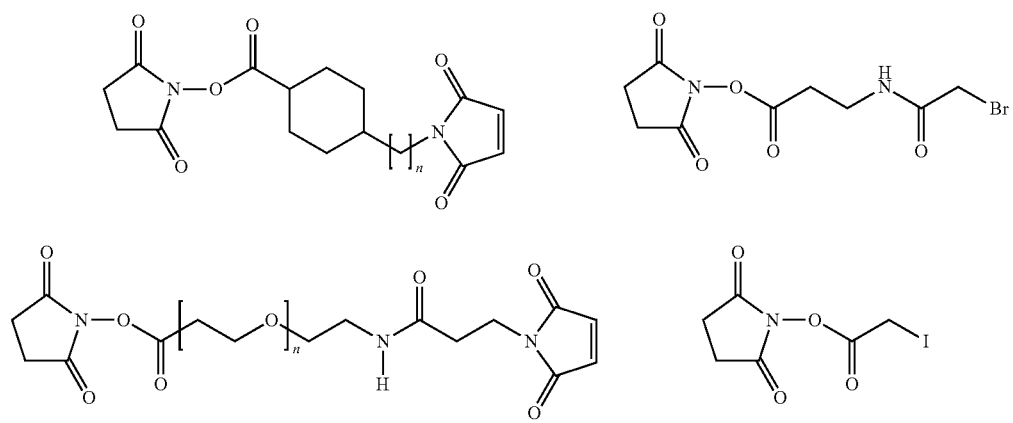

TABLE 1-continued

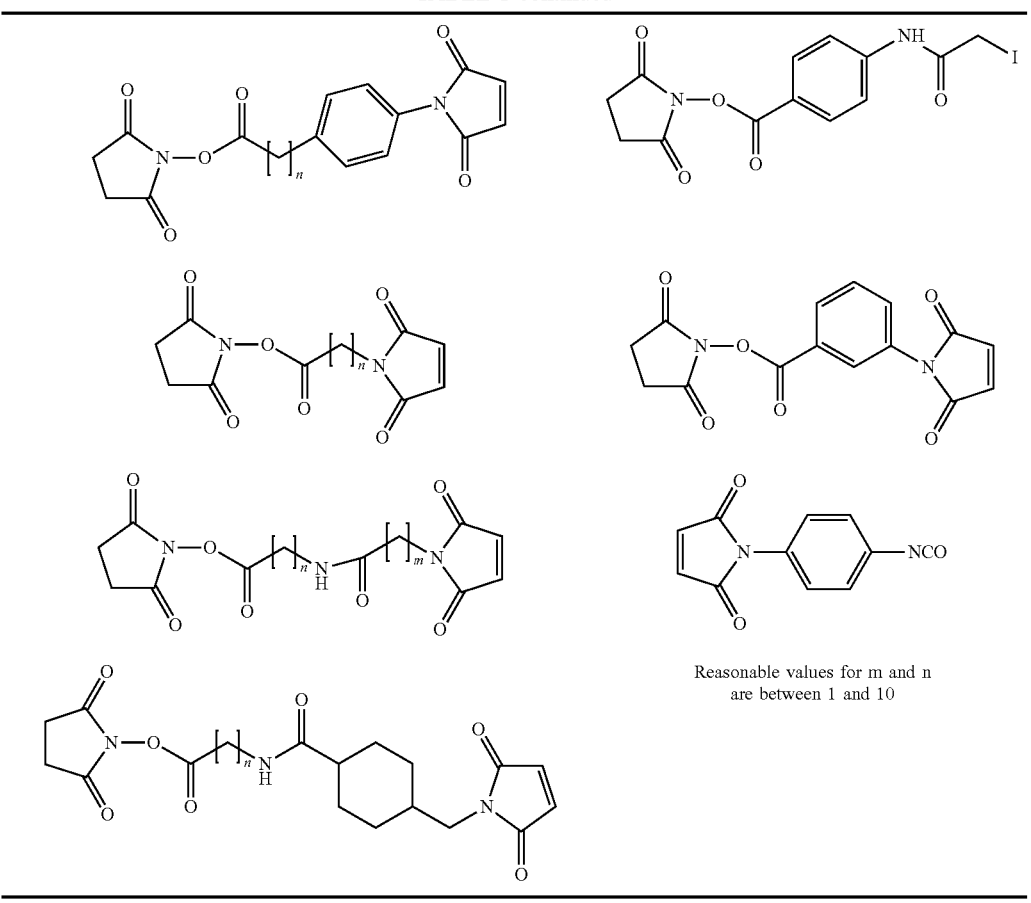

Reasonable values for m and n are between 1 and 10

Direct coupling of the amine on the hapten and a carboxylic acid functionality on the spacer building block in the presence of a coupling agent may also be used as a mode of attachment. Preferred reagents are those typically used in peptide synthesis. Peptide coupling reagents include but are not limited to O-(Benzotriazol-1-yl)-N,N,N',N'-tetramethyluronium tetrafluoroborate (TBTU, CAS #125700-67-6), see: Pruhs, S., Org. Process. Res. Dev. 2006, 10:441; N-Hydroxybenzotriazole (HOBT, CAS #2592-95-2) with a carbodiimide dehydrating agent, for example N—N-dicyclohexylcarbodiimide (DCC), diisopropylcarbodiimide (DIC), or 1-ethyl-3(3-dimethylaminopropyl)carbodiimidehydrochloride (EDC), see: König W., Geiger, R. Chem. Ber., 1970, 103 (3):788; 3-(diethoxyphosphoryloxy)-1,2,3-benzotrazin-4(3H)-one (DEPBT, CAS#165534-43-0), see: Liu, H. et. al., Chinese Chemical Letters, 2002, 13(7):601; Bis(2-oxo-3-oxazolidinyl)phosphonic chloride; (BOP-Cl, CAS#68641-49-6), see: Diago-Meseguer, J et. al. Synthesis, 1980, 7:547-51 and others described in detail by Benoiton in Chemistry of Peptide Synthesis, CRC Press, Boca Raton, Fla., 2005, Chapter 2, and the technical bulletin provided by Advanced Automated Peptide Protein Technologies (aapptec), 6309 Shepardsville Rd., Louisville Ky. 40228, ph 888 692 9111; www.aapptec.com, and references within. These methods create a stable amide linkage attaching the hapten to the spacer. Examples of spacers that can be obtained using known methods and attached to amino-bearing haptens utilizing routine optimization of reaction conditions employing the methods described and cited above are shown, but not limited to those in Table 2. These spacers allow attachment of the hapten to a thiol group on a carrier.

TABLE 2

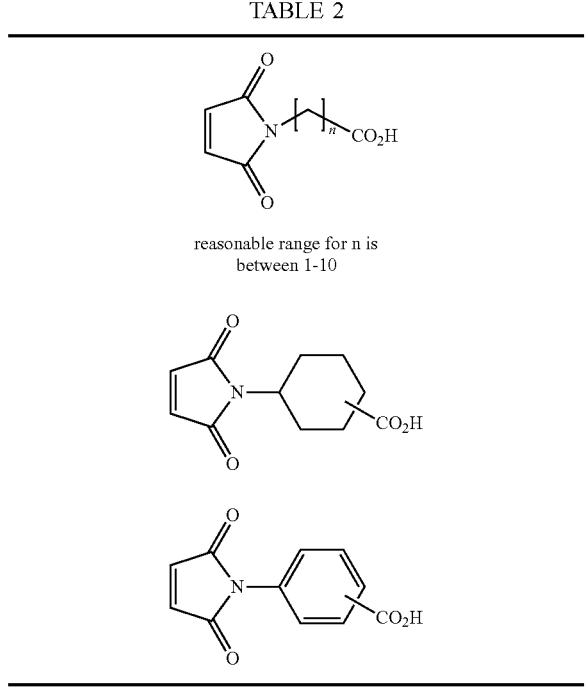

reasonable range for n is between 1-10

Spacers may also be constructed in a step-wise fashion by sequential attachment of appropriate chemical groups to the hapten including the step of forming the functional linking group that is capable of binding to the carrier. See illustrative examples under General Reaction Schemes.

Additionally, when the hapten has a nucleophilic group, for example a thiol group, an amino group or a hydroxyl group which will become the point of attachment of the spacer, the spacer may also be constructed by alkylation of the thiol, amine or hydroxyl group. Any alkyl group that is appropriately substituted with a moiety capable of undergoing a substitution reaction, for example, an alkyl halide, or sulfonic acid ester such as p-Toluenesulfonate, may be used to attach the spacer. Many examples of alkylation reactions are known to one skilled in the art and specific examples may be found in the general chemical literature and optimized through routine experimentation. A discussion of alkylation reactions with many references can be found in Chapter 10 of *March's Advanced Organic Chemistry*, Smith, M. B., and March, J., John Wiley & sons, Inc. NY, 2001. Other linkages may also be employed such as reaction of the nucleophilic moiety, for example an amine, on the hapten with an isocyanate to form a urea or reaction with an isothiocyanate to form a thiourea linkage, see: Li, Z., et. al., *Phosphorus, Sulfur and Silicon and the Related Elements*, 2003, 178(2):293-297. Spacers may be attached to haptens bearing hydroxyl groups via reaction with isocyanate groups to form carbamate or urethane linkages. The spacer may be differentially activated with the isocyanate functional group on one end and a functional linking group capable of reacting with the carrier, see: Annunziato, M. E., Patel, U.S., Ranade, M. and Palumbo, P. S., *Bioconjugate Chem.*, 1993, 4:212-218.

For haptens bearing a carboxylic acid group, modes of attachment of a spacer portion to the hapten include activation of the carboxylic acid group as an acyl halide or active ester, examples of which are shown in Table 3, preparation of which are described previously, followed by reaction with an amino (—NH$_2$—), hydrazino (—NH—NH$_2$—), hydrazido (—C(O)—NH—NH$_2$—) or hydroxyl group (—OH) on the spacer portion to form an amide, hydrazide, diacylhydrazine or ester linkage, or direct coupling of the carboxylic acid group with an amino group on the spacer portion or directly on the carrier with a peptide coupling reagent and/or carbodiimide dehydrating reagent, described previously, examples of which are shown in Tables 4 and 5. Procedures found in references cited previously for formation of activated esters and use of peptide coupling agents may be employed for attachment of carboxylic acid-bearing haptens to spacer building blocks and protein carriers with available amino groups utilizing routine optimization of reaction conditions.

TABLE 3

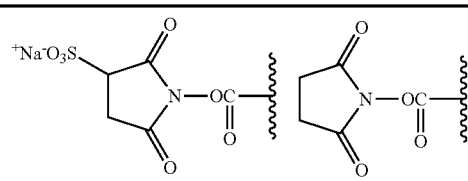

Sulfo NHS and NHS

TABLE 3-continued

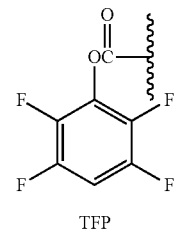

TFP

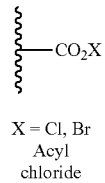

X = Cl, Br
Acyl chloride

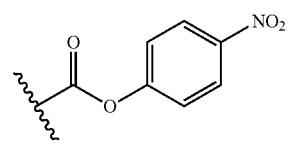

PNP

TABLE 4

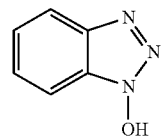

HOBT

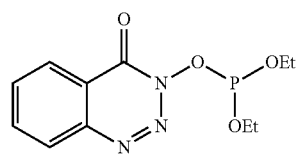

DEPT

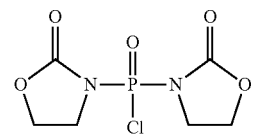

BOP-Cl

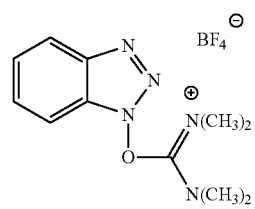

TBTU

TABLE 5

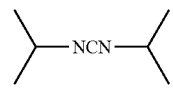

diisopropylcarbodiimide
(DIC)

Dicyclohexylcarbodiimide
(DCC)

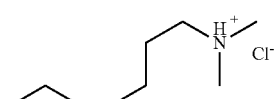

1-ethyl-3(3-
dimethylaminopropyl)carbodiimide.HCl
(EDC)

Other electrophilic groups may be present on the hapten to attach the spacer, for example, a sulfonyl halide

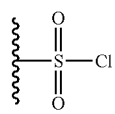

or electrophilic phosphorous group, for example:

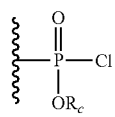

See: Malachowski, William P., Coward, James K., *Journal of Organic Chemistry*, 1994, 59 (25):7616 or:

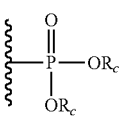

$R_c$ is alkyl, cycloalkyl, aryl, substituted aryl, aralkyl.
See: Aliouane, L., et. al, *Tetrahedron Letters*, 2011, 52(28): 8681.

Haptens that bear aldehyde or ketone groups may be attached to spacers using methods including but not limited to reaction with a hydrazide group $H_2N-NH-C(O)-$ on the spacer to form an acylhydrazone, see: Chamow, S. M., Kogan, T. P., Peers, D. H., Hastings, R. C., Byrn, R. A. and Askenaszi, A., *J. Biol. Chem.*, 1992, 267(22): 15916. Examples of bifunctional hydrazide spacer groups that allow attachment to a thiol group on the carrier are shown in Table 6.

TABLE 6

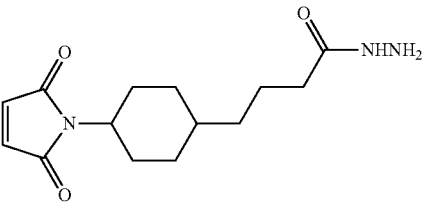 [SMILES: NNC(=O)CCCC1CCC(N2C(=O)C=CC2=O)CC1]

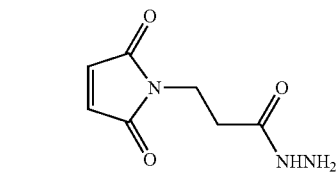 [SMILES: NNC(=O)CCN1C(=O)C=CC1=O]

Haptens may also contain thiol groups which may be reacted with the carrier provided that the carrier has been modified to provide a group that may react with the thiol. Carrier groups may be modified by methods including but not limited to attachment of a group containing a maleimide functional group by reaction of an amino group on the carrier with N-Succinimidyl maleimidoacetate, (AMAS, CAS #55750-61-3), Succinimidyl iodoacetate (CAS#151199-81-4), or any of the bifunctional spacer groups shown in Table 1 to introduce a group which may undergo a reaction resulting in attachment of the hapten to the carrier.

The functional linking group capable of forming a bond with the carrier may be any group capable of forming a stable linkage and may be reactive to a number of different groups on the carrier. The functional linking group may preferably react with an amino group, a carboxylic acid group or a thiol group on the carrier, or derivative thereof. Non-limiting examples of the functional linking group are a carboxylic acid group, acyl halide, active ester (as defined previously), isocyanate, isothiocyanate, alkyl halide, amino group, thiol group, maleimide group, acrylate group ($H_2C=CH-C(O)-$) or vinyl sulfone group $H_2C=CH-SO_2-$) See: Park, J. W., et. al., *Bioconjugate Chem.*, 2012, 23(3): 350. The functional linking group may be present as part of a differentially activated spacer building block that may be reacted stepwise with the hapten and the resulting hapten derivative may then be reacted with the carrier. Alternatively, the hapten may be derivatized with a spacer that bears a precursor group that may be transformed into the functional linking group by a subsequent reaction. When the functional linking group on the spacer is an amine or a carboxylic acid group, the coupling reaction with the carboxylic acid group or amine on the carrier may be carried out directly through the use of peptide coupling reagents according to procedures in the references cited above for these reagents.

Particular disulfide groups, for example, pyridyldisulfides, may be used as the functional linking group on the spacer which may undergo exchange with a thiol group on the carrier to from a mixed disulfide linkage, see: Ghetie, V., et al., *Bioconjugate Chem.*, 1990, 1:24-31. These spacers may be attached by reaction of the amine-bearing hapten with an active ester which is attached to a spacer bearing the pyridyldisulfide group, examples of which include but are not limited to those shown in Table 7.

TABLE 7

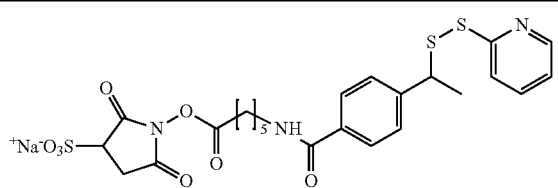

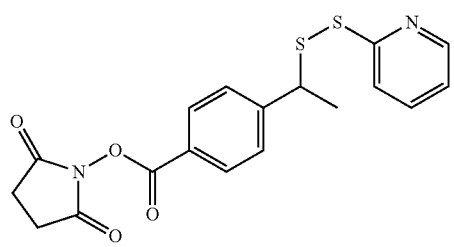 [SMILES: CC(SSc1ccccn1)c1ccc(C(=O)ON2C(=O)CCC2=O)cc1]

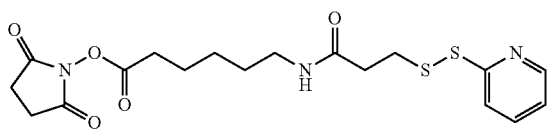 [SMILES: O=C(CCSSc1ccccn1)NCCCCCC(=O)ON1C(=O)CCC1=O]

TABLE 7-continued

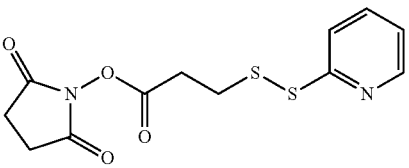 [SMILES: O=C(CCSSc1ccccn1)ON1C(=O)CCC1=O]

Most often the carrier is a protein and the 8-amino groups of the lysine residues may be used for attachment, either directly by reaction with an amine-reactive functional linking group or after derivitization with a thiol-containing group, including N-Succinimidyl S-Acetylthioacetate, (SATA, CAS 76931-93-6), or an analogue thereof, followed by cleavage of the actetate group with hydroxylamine to expose the thiol group for reaction with the functional linking group on the hapten. Thiol groups may also be introduced into the carrier by reduction of disulfide bonds within protein carriers with mild reducing reagents including but not limited to 2-mercaptoethylamine, see: Bilah, M., et. al., *Bioelectrochemistry*, 2010, 80(1):49, phosphine reagents, see: Kirley, T. L., *Analytical Biochemistry*, 1989, 180(2):231 or dithioerythritol (DTT, CAS 3483-12-3) Cleland, W., *Biochemistry*, 1964, 3:480-482.

General Reaction Schemes

Representative compounds of the present invention can be synthesized in accordance with the general synthetic methods described below. Compounds of Formula I can be prepared by methods known to those who are skilled in the art. The following reaction schemes are only meant to represent examples of the invention and are in no way meant to be a limit of the invention.

Scheme 1

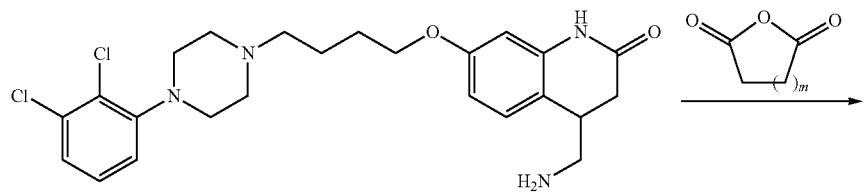

Example 1

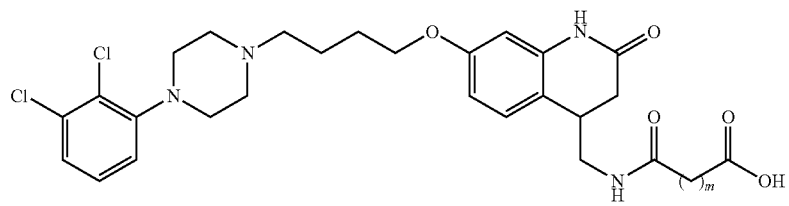

The hapten of Example 1 may be elaborated with spacers by reaction with a cyclic anhydride compound, such as succinic anhydride or glutaric anhydride, as shown in Scheme 1. The reaction may be carried out in a solvent such as THF, at room temperature, overnight.

Scheme 2

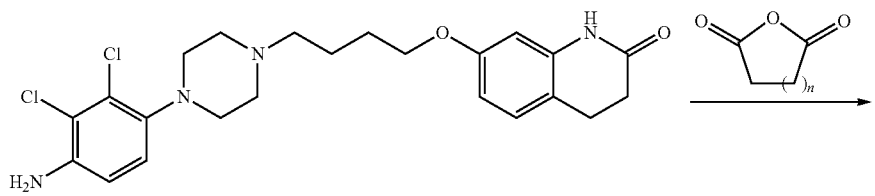

Example 2

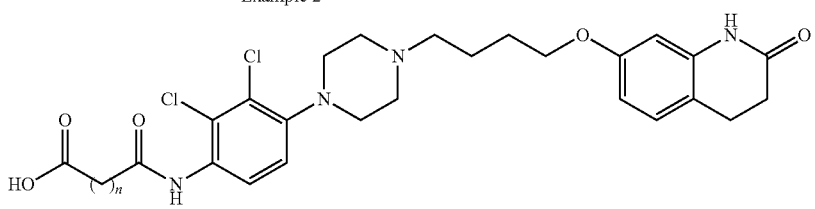

The hapten of Example 2 may be elaborated with spacers by reaction with a cyclic anhydride compound, such as succinic anhydride or glutaric anhydride, as shown in Scheme 2. The reaction may be carried out in a solvent such as pyridine, and heated to about 110° C. in a microwave oven for 3-6 hours.

Scheme 3

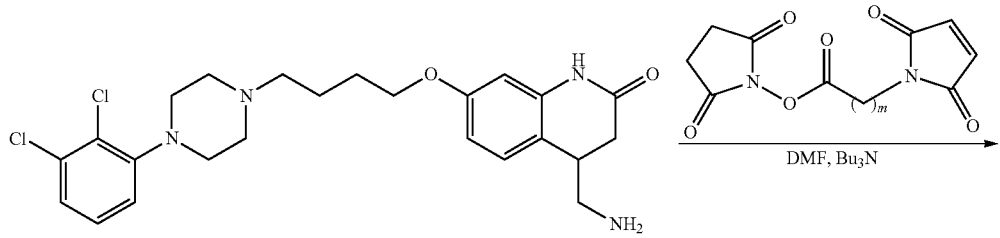

Example 1

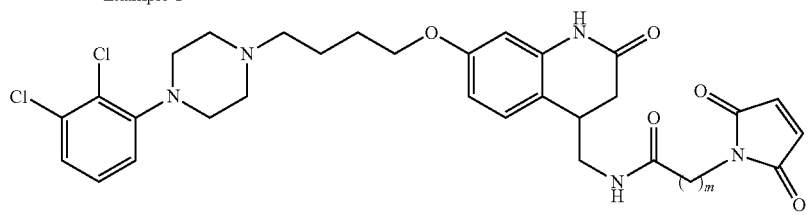

Haptens which terminate in an alkyl amine group, such as Example 1 may be further functionalized with a maleimide group. Those skilled in the art will recognize that the same methodology will be applicable to other alkyl amino derivatives of aripiprazole. Reaction of the aripiprazole derived amine with alkyl-maleimide functionalizing group, such as 2,5-dioxopyrrolidin-1-yl 2-(2,5-dioxo-2,5-dihydro-1H-pyrrol-1-yl)acetate, in a solvent such as DMF, in the presence of a base, such as tributyl amine, at 20° C., for one hour generates haptens of aripiprazole with a maleimide spacer.

Scheme 4

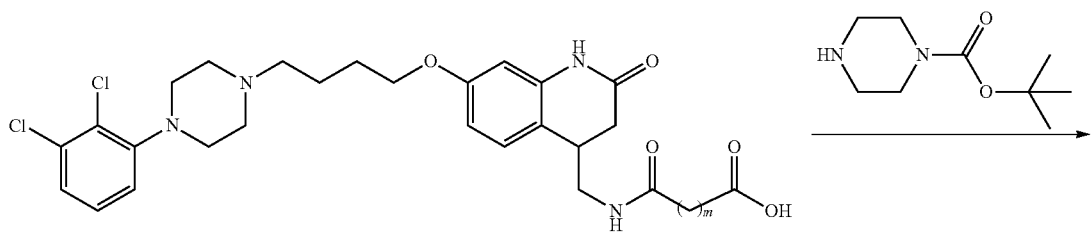

-continued

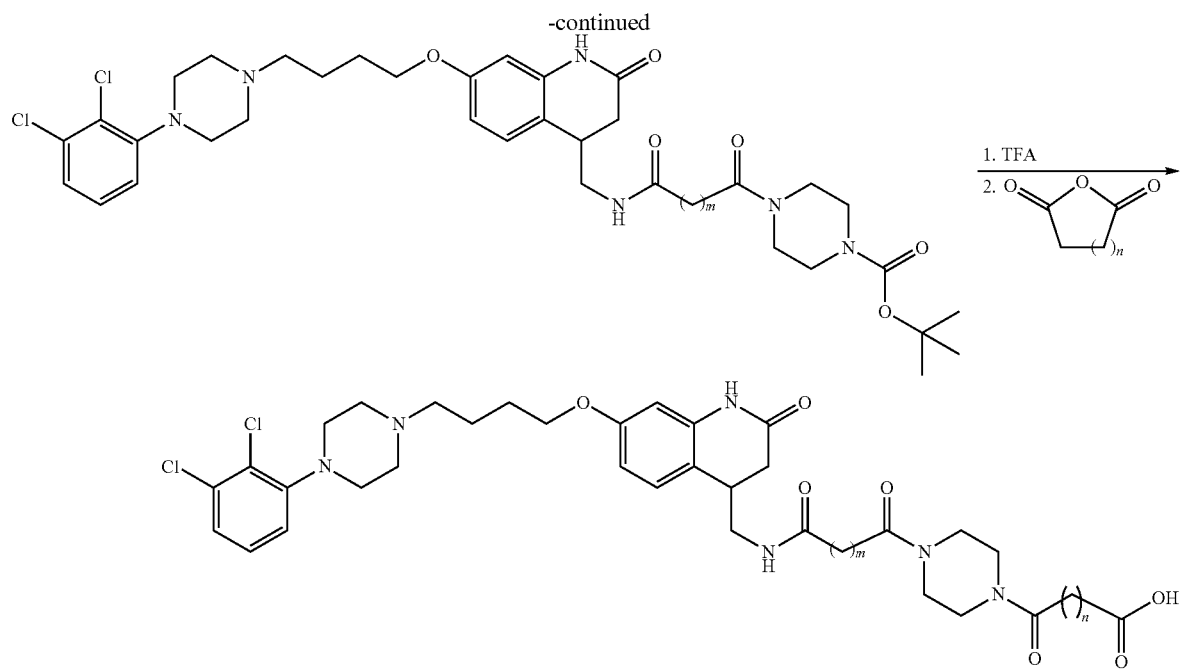

Spacers on haptens may be extended as shown in Scheme 4. Haptens with spacers bearing a carboxylic acid functionality may be dissolved in a suitable solvent, such as dichloromethane, under inert atmosphere, and treated with N-t-butoxycarbonylpiperazine and an appropriate base, such as diisopropylethylamine. The solution may then be treated with diethyl cyanophosphonate to install a piperazine moiety onto the spacer. Deprotection of the piperazine may be accomplished with trifluoroacetic acid or other methods known in the art. Reaction with a cyclic anhydride gives compounds of Formula I where $R^1$ is

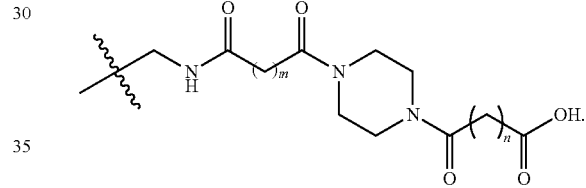

Scheme 5

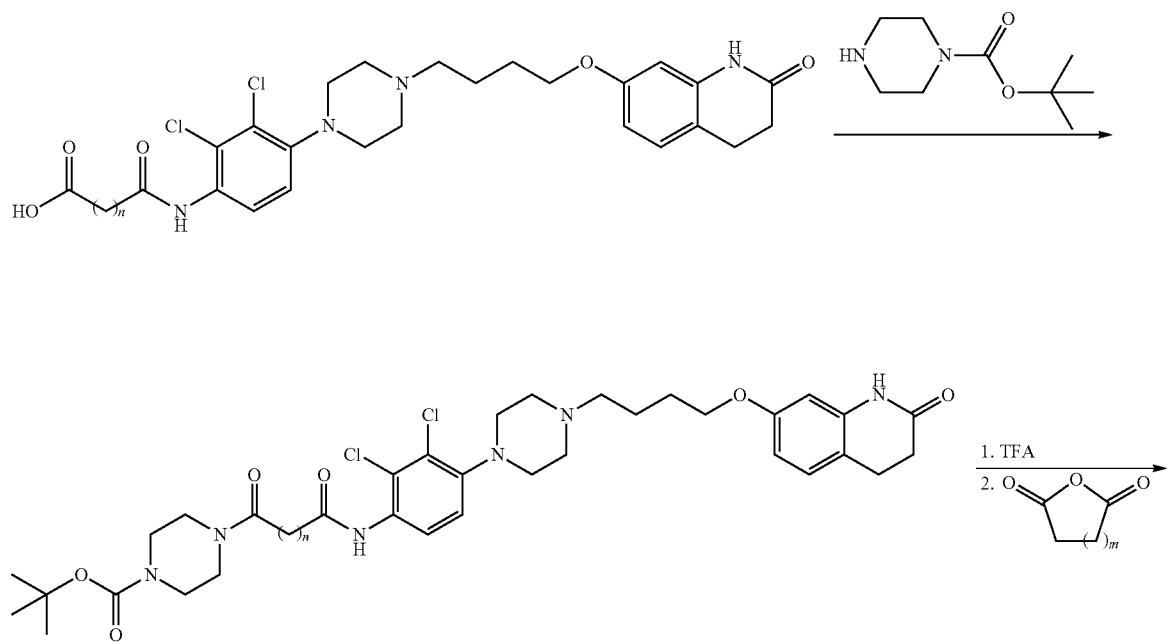

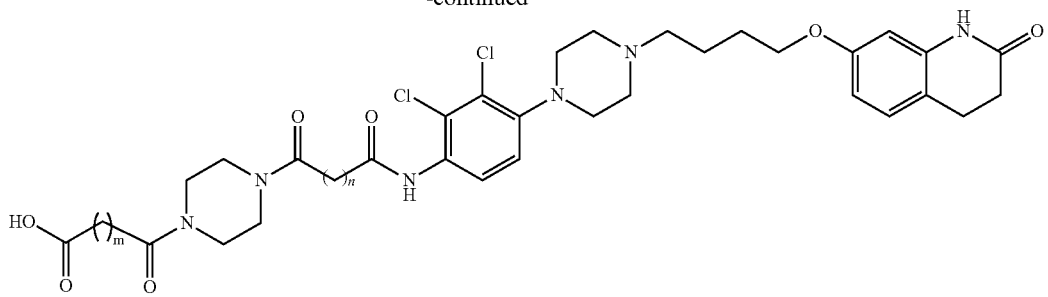

Spacers on haptens may also be extended as shown in Scheme 5. Haptens with spacers bearing carboxylic acid functionality may be dissolved in a suitable solvent, such as dichloromethane, under inert atmosphere, and treated with N-t-butoxycarbonylpiperazine and an appropriate base, such as diisopropylethylamine. The solution may then be treated with diethyl cyanophosphonate to install a piperazine moiety onto the spacer. Deprotection of the piperazine may be accomplished with trifluoroacetic acid or other methods known in the art. Reaction with a cyclic anhydride gives compounds of Formula I where $R^2$ is

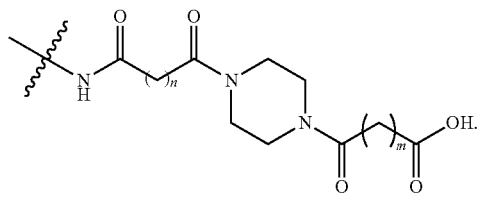

Haptens may also be generated directly from the parent molecule aripiprazole by either acylation or alkylation of the quinolinone nitrogen. Scheme 6 depicts a synthetic route in which an acyl group may be appended to aripiprazole by reaction with the acid chloride of 4-chlorobutyric acid using N,N-dimethyl-4-aminopyridine (DMAP) as a catalyst in the presence of a base such as pyridine in an aprotic solvent, for example N,N-dimethylformamide, see: Example 5, US20110230520. Nucleophilic substitution of the chloride by N-methyl-β-alanine methyl ester may be carried out in the presence of sodium iodide and a base, for example potassium carbonate in a dipolar aprotic solvent such as N,N-dimethylformamide, see: Penning, T., D., et. al., *J. Med Chem*, 2002, 45:3482. Hydrolysis of the ester group using standard methods known to one skilled in the art, such as exposure to aqueous base, yields a carboxy-functionalized hapten which may be further elaborated using the methods described previously, one example of which is depicted in Scheme 9 below, to provide a suitably functionalized compound for attachment to an immunogenic carrier.

Scheme 6

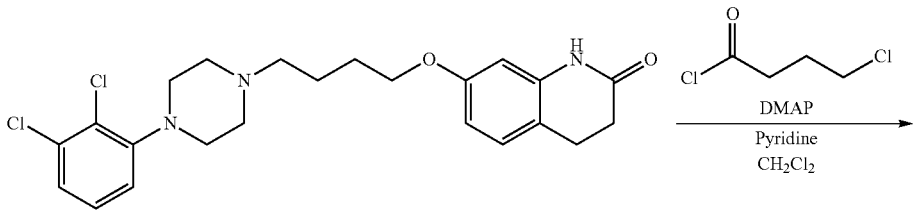

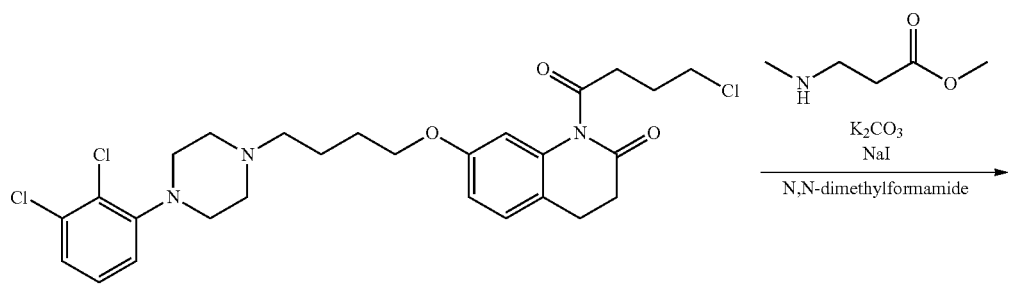

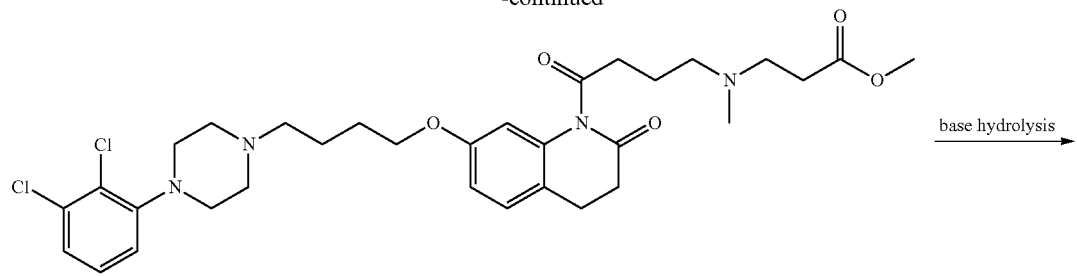

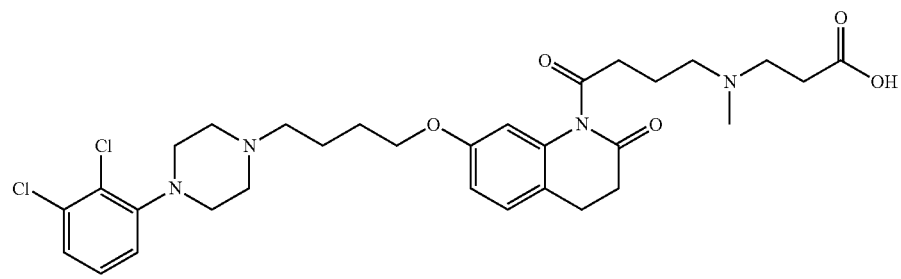

Scheme 7 illustrates a mode of attachment of an alkyl group to the nitrogen of the quinolinone group of aripiprazole using standard alkylation chemistry. An iodo compound, for example methyl-4-iodobutyrate may be reacted with aripiprazole in the presence of a base such as cesium carbonate in a dipolar aprotic solvent such as N,N-dimethylformamide using the method of Example 6 in US20120004165. Hydrolysis of the ester group using standard methods known to one skilled in the art, such as exposure to aqueous base, yields a carboxy-functionalized hapten which may be further elaborated using the methods described previously, one example of which is depicted in Scheme 9 below, to provide a suitably functionalized compound for attachment to an immunogenic carrier.

Scheme 7

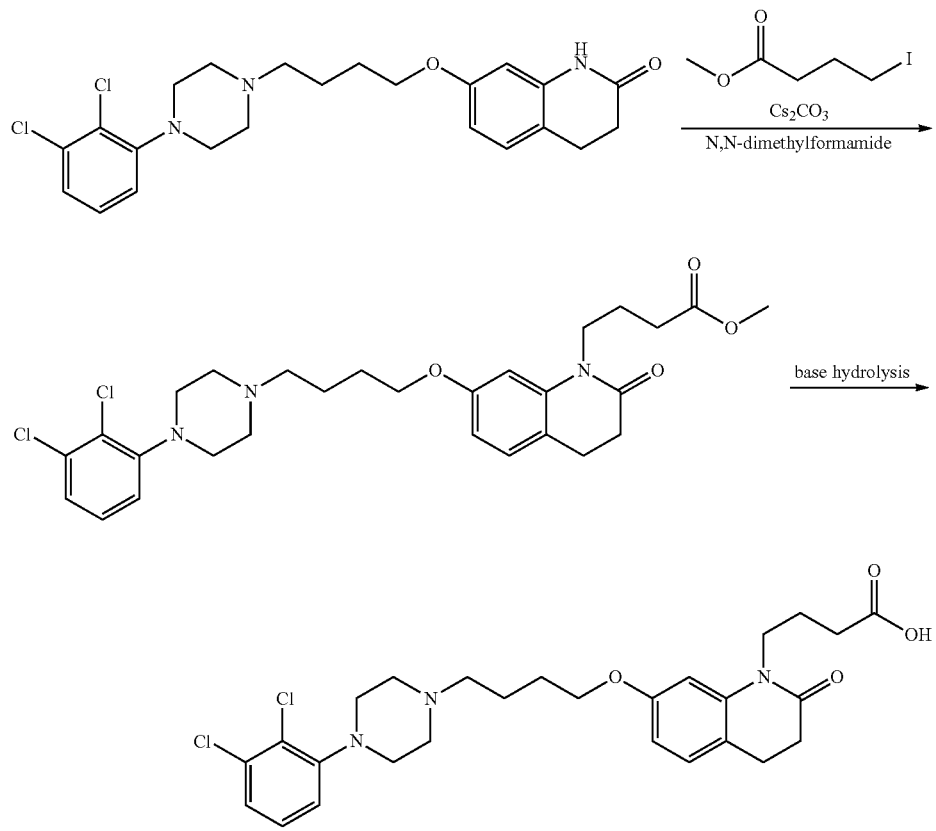

Scheme 8

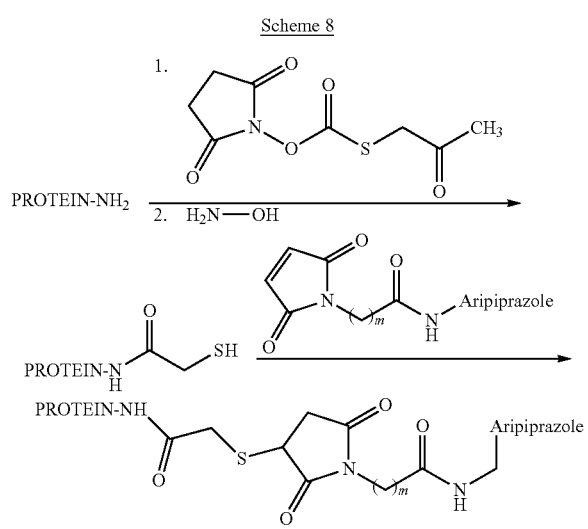

Maleimide functionalized haptens may be conjugated to proteins according to the method shown in Scheme 8. Activation of protein lysine residues by acylation of the epsilon-nitrogen with N-succinimidyl S-acetylthioacetate (SATA), followed by subsequent hydrolysis of the S-acetyl group with hydroxylamine produces a nucleophilic sulfhydryl group. Conjugation of the sulfhydryl activated protein with the maleimide derivatized hapten (prepared as described in general Scheme 3) proceeds via a Michael addition reaction. Suitable proteins are known to those skilled in the art and include keyhole limpet hemocyanin, bovine thyroglobulin, and ovalbumin. While Scheme 8 illustrates protein-hapten conjugation where $R^1$ is

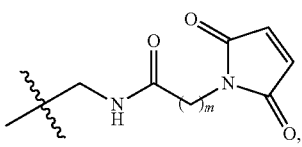

the same chemistry can be used to conjugate any maleimide functionalized hapten to a protein.

Scheme 9

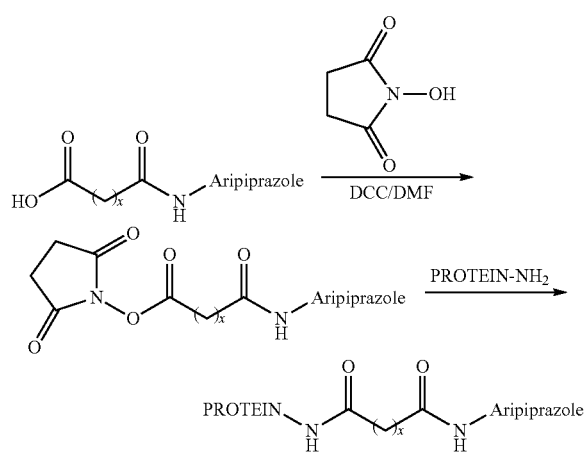

where x is m or n, as defined in Formula I.

Carboxylic acid functionalized haptens may be conjugated to proteins according to the method shown in Scheme 9. Reaction with N-hydroxysuccinimide and a suitable coupling agent, such as dicyclohexylcarbodiimide (DCC) and a base such as tributylamine, in a solvent such as DMF at a temperature of about 20° C., for about 18 hours, activates the carboxylic acid with the hydroxypyrrolidine-2,5-dione leaving group. The activated spacer and hapten may then be conjugated to a protein in a solvent, such as pH 7.5 phosphate buffer, at about 20° C. for about 2.5 hours. Suitable proteins are known to those skilled in the art and include keyhole limpet hemocyanin, bovine thyroglobulin, and ovalbumin. While Scheme 9 illustrates protein-hapten conjugation where $R^2$ is $NHC(O)(CH_2)_nCO_2H$, the same chemistry can be used to conjugate any $CO_2H$ functionalized hapten to a protein.

Antibody Production

The conjugates above are useful for the production of antibodies which bind the anti-psychotic drug to which they were generated (aripiprazole). These antibodies can be used in assays to detect the presence and/or amount of the anti-psychotic drug in patient samples. Such detection permits therapeutic drug monitoring enabling all of the benefits thereof. Detection of levels of anti-psychotic drugs may be useful for many purposes, including: detection in combination with the detection of other anti-psychotic drugs, including those selected from the group consisting of risperidone, paliperidone, quetiapine, olanzapine, and metabolites thereof, such detection permitting the simultaneous measurement of these anti-psychotic drugs; determination of patient adherence or compliance with prescribed therapy; use as a decision tool to determine whether a patient should be converted from an oral anti-psychotic regimen to a long-acting injectable anti-psychotic regimen; use as a decision tool to determine if the dose level or dosing interval of oral or injectable anti-psychotics should be increased or decreased to ensure attainment or maintenance of efficacious or safe drug levels; use as an aid in the initiation of anti-psychotic drug therapy by providing evidence of the attainment of minimum pK levels; use to determine bioequivalence of anti-psychotic drug in multiple formulations or from multiple sources; use to assess the impact of polypharmacy and potential drug-drug interactions; and use as an indication that a patient should be excluded from or included in a clinical trial and as an aid in the subsequent monitoring of adherence to clinical trial medication requirements.

Having provided the conjugates of the subject invention, which comprise the compounds herein and an immunogenic carrier, antibodies can be generated, e.g., polyclonal, monoclonal, chimeric, and humanized antibodies, that bind to the anti-psychotic drug. Such antibodies that are particularly contemplated include monoclonal and polyclonal antibodies as well as fragments thereof, e.g., recombinant proteins, containing the antigen-binding domain and/or one or more complementarity determining regions of these antibodies. Preferably, the antibody will bind to the drug and any desired pharmacologically active metabolites. By altering the location of the attachment of the immunogenic carrier to the compounds of the invention, selectivity and cross-reactivity with metabolites can be engineered into the antibodies. For aripiprazole, cross-reactivity with dehydroaripiprazole may be desirable. Antibodies may be generated that detect both aripiprazole and dehydroaripiprazole, or antibodies may be generated that detect each separately (thus defining the antibody "specific binding" properties). An antibody specifically binds one or more compounds when its binding of the one or more compounds is equimolar or substantially equimolar.

Methods of producing such antibodies comprise inoculating a host with the conjugate (the compound and the immunogenic carrier being an immunogen) embodying features of the present invention. Suitable hosts include, but are not limited to, mice, rats, hamsters, guinea pigs, rabbits, chickens, donkeys, horses, monkeys, chimpanzees, orangutans, gorillas, humans, and any species capable of mounting a mature immune response. The immunization procedures are well established in the art and are set forth in numerous treatises and publications including "*The Immunoassay Handbook*", 2nd Edition, edited by David Wild (Nature Publishing Group, 2000) and the references cited therein.

Preferably, an immunogen embodying features of the present invention is administered to a host subject, e.g., an animal or human, in combination with an adjuvant. Suitable adjuvants include, but are not limited to, Freund's adjuvant, powdered aluminum hydroxide (alum), aluminum hydroxide together with *Bordetella pertussis*, and monophosphoryl lipid A-synthetic trehalose dicorynomycolate (MPL-TDM).

Polyclonal antibodies can be raised in a mammalian host by one or more injections of an immunogen which can optionally be administered together with an adjuvant. Typically, an immunogen or a combination of an immunogen and an adjuvant is injected into a mammalian host by one or multiple subcutaneous or intraperitoneal injections. Preferably, the immunization program is carried out over at least one week, and more preferably, over two or more weeks. Polyclonal antibodies produced in this manner can be isolated and purified utilizing methods well know in the art.

Monoclonal antibodies can be produced by the well-established hybridoma methods of Kohler and Milstein, e.g., *Nature* 256:495-497 (1975). Hybridoma methods typically involve immunizing a host or lymphocytes from a host, harvesting the monoclonal antibody secreting or having the potential to secrete lymphocytes, fusing the lymphocytes to immortalized cells, and selecting cells that secrete the desired monoclonal antibody.

A host can be immunized to elicit lymphocytes that produce or are capable of producing antibodies specific for an immunogen. Alternatively, the lymphocytes can be immunized in vitro. If human cells are desired, peripheral blood lymphocytes can be used, although spleen cells or lymphocytes from other mammalian sources are preferred.

The lymphocytes can be fused with an immortalized cell line to form hybridoma cells, a process which can be facilitated by the use of a fusing agent, e.g., polyethylene glycol. By way of illustration, mutant rodent, bovine, or human myeloma cells immortalized by transformation can be used. Substantially pure populations of hybridoma cells, as opposed to unfused immortalized cells, are preferred. Thus, following fusion, the cells can be grown in a suitable medium that inhibits the growh or survival of unfused, immortalized cells, for example, by using mutant myeloma cells that lack the enzyme hypoxanthine guanine phosphoribosyl transferase (HGPRT). In such an instance, hypoxanthine, aminopterin, and thymidine can be added to the medium (HAT medium) to prevent the growth of HGPRT-deficient cells while permitting hybridomas to grow.

Preferably, immortalized cells fuse efficiently, can be isolated from mixed populations by selection in a medium such as HAT, and support stable and high-level expression of antibody following fusion. Preferred immortalized cell lines include myeloma cell lines available from the American Type Culture Collection, Manassas, Va.

Because hybridoma cells typically secrete antibody extracellularly, the culture media can be assayed for the presence of monoclonal antibodies specific for the anti-psychotic drug. Immunoprecipitation of in vitro binding assays, for example, radiioimmunoassay (RIA) or enzyme-linked immunosorbent assay (ELISA), can be used to measure the binding specificity of monoclonal antibodies.

Monoclonal antibody-secreting hybridoma cells can be isolated as single clones by limiting dilution procedures and sub-cultured. Suitable culture media include, but are not limited to, Dulbecco's Modified Eagle's Medium, RPMI-1640, and polypeptide-free, polypeptide-reduced, or serum-free media, e.g., Ultra DOMA PF or HL-1, available from Biowhittaker, Walkersville, Md. Alternatively, the hybridoma cells can be grown in vivo as ascites.

Monoclonal antibodies can be isolated and/or purified from a culture medium or ascites fluid by conventional immunoglobulin (Ig) purification procedures including, but not limited to, polypeptide A-SEPHAROSE, hydroxylapatite chromatography, gel electrophoresis, dialysis, ammonium sulfate precipitation, and affinity chromatography.

Monoclonal antibodies can also be produced by recombinant methods such as are described in U.S. Pat. No. 4,166,452. DNA encoding monoclonal antibodies can be isolated and sequenced using conventional procedures, e.g., using oligonucleotide probes that specifically bind to murine heavy and light antibody chain genes, preferably to probe DNA isolated from monoclonal antibody hybridoma cells lines secreting antibodies specific for anti-psychotic drugs.

Immunoassays

The antibodies thus produced can be used in immunoassays to recognize/bind to the anti-psychotic drug, thereby detecting the presence and/or amount of the drug in a patient sample. Preferably, the assay format is a competitive immunoassay format. Such an assay format and other assays are described, among other places, in Hampton et al. (*Serological Methods, A Laboratory Manual*, APS Press, St. Paul, Minn. 1990) and Maddox et al. (*J. Exp. Med.* 158:12111, 1983).

A reagent kit can also be provided comprising an antibody as described above. A representative reagent kit may comprise an antibody that binds to the anti-psychotic drug, aripiprazole, a complex comprising an analog of an anti-psychotic drug or a derivative thereof coupled to a labeling moiety, and may optionally also comprise one or more calibrators comprising a known amount of an anti-psychotic drug or a related standard.

As noted above, reagent kits may comprise calibrators and/or control materials which comprise a known amount of the analyte to be measured. The concentration of the analyte can be calculated by comparing results obtained for a sample with resulted obtained for a standard. A calibration curve can be constructed and used for relating the sets of results and for determining the concentration of an analyte in a sample.

Any sample that is suspected of containing an analyte, e.g., an anti-psychotic drug, can be analyzed in accordance with the methods of the presently preferred embodiments. The sample can be pretreated if desired and can be prepared in any convenient medium that does not interfere with the assay. Preferably, the sample comprises an aqueous medium such as a body fluid from a host, most preferably plasma or serum.

Applications entitled "Haptens of Aripiprazole", U.S. Provisional Patent Appl. No. 61/691,450, filed Aug. 21, 2012, and US 20140163206, filed Aug. 20, 2013), "Haptens of Olanzapine", U.S. Provisional Patent Appl. No. 61/691,454, filed Aug. 21, 2012, and US 20140213766, filed Aug. 20, 2013), "Haptens of Paliperidone", U.S. Provisional Patent Appl. No. 61/691,459, filed Aug. 21, 2012 and US 2014/0213767, filed Aug. 20, 2013), "Haptens of Quetiapine", U.S. Provisional Patent Appl. No. 61/691,462, filed Aug. 21, 2012, and US 20140221616, filed Aug. 20, 2013), "Haptens of Risperidone and Paliperidone", U.S. Provisional Patent Appl. No. 61/691,469, filed Aug. 21, 2012, and US 20140155585, Aug. 20, 2013), "Antibodies to Aripiprazole Haptens and Use Thereof", U.S. Provisional Patent Appl. No. 61/691,544, filed Aug. 21, 2012, and US 20140057299, filed Aug. 20, 2013), "Antibodies to Olanzapine Haptens and Use Thereof", U.S. Provisional Patent Appl. No. 61/691,572, filed Aug. 21, 2012, US 20140057303, filed Aug. 20, 2013), "Antibodies to Paliperidone Haptens and Use Thereof", U.S. Provisional Patent Appl. No. 61/691,634, filed Aug. 21, 2012, and US 20140057297, filed Aug. 20, 2013), "Antibodies to Quetiapine Haptens and Use Thereof", U.S. Provisional Patent Appl. No. 61/691,598, filed Aug. 21, 2012, and US 20140057305, filed Aug. 20, 2013), "Antibodies to Risperidone Haptens and Use Thereof", U.S. Provisional Patent Appl. No. 61/691,615, filed Aug. 21, 2012, and US 20140057301, filed Aug. 20, 2013), "Antibodies to Aripiprazole and Use Thereof", U.S. Provisional Patent Appl. No. 61/691,522, filed Aug. 21, 2012, and US 20140057300, filed Aug. 20, 2013), "Antibodies to Olanzapine and Use Thereof", U.S. Provisional Patent Appl. No. 61/691,645, filed Aug. 21, 2012, and US 20140057304, filed Aug. 20, 2013), "Antibodies to Paliperidone and Use Thereof", U.S. Provisional Patent Appl. No. 61/691,692, filed Aug. 21, 2012, and US 20140057298, filed Aug. 20, 2013), "Antibodies to Quetiapine and Use Thereof", U.S. Provisional Patent Appl. No. 61/691,659, filed Aug. 21, 2012, and US 20140057306, filed Aug. 20, 2013), and "Antibodies to Risperidone and Use Thereof", U.S. Provisional Patent Appl. No. 61/691,675, filed Aug. 21, 2012, and US 20140057302, filed Aug. 20, 2013) are all incorporated herein by reference in their entireties.

EXAMPLES

Representative compounds of the present invention can be synthesized in accordance with the general synthetic methods described below. Compounds of Formula (I) can be prepared by methods known to those who are skilled in the art. The following examples are only meant to represent examples of the invention and are in no way meant to be a limit of the invention.

Example 1

4-(aminomethyl)-7-(4-(4-(2,3-dichlorophenyl)piperazin-1-yl)butoxy)-3,4-dihydroquinolin-2(1H)-one

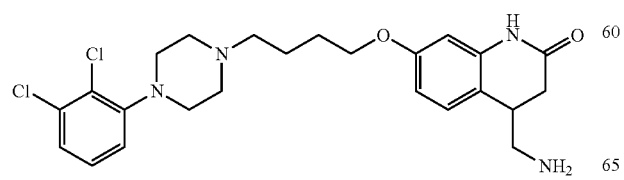

Step A 1-(bromomethyl)-4-methoxy-2-nitrobenzene

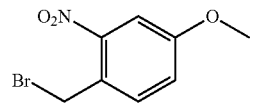

To a well-stirred solution of compound 4-methoxy-1-methyl-2-nitrobenzene (218 g, 1.30 mol) in $CCl_4$ (1500 mL) was added AIBN (21.7 g, 0.13 mol), and NBS (348 g, 1.96 mol). After the reaction mixture was heated at reflux for 16 h under $N_2$, water was added and the product extracted from the aqueous phase with $CH_2Cl_2$. The resultant organic phase was washed with brine, dried over $Na_2SO_4$ and the solvent was evaporated to give a solid which was purified by silica gel chromatography (eluting with petroleum ether/ethyl acetate, 20:1) to the title compound as a yellow solid. ESI-MS (M+1) 246. $^1$H NMR: ($CDCl_3$, 400 MHz): δ (ppm) 7.55 (s, 1H), 7.46-7.42 (d, 1H), 7.14-7.11 (d, 1H), 4.79 (s, 2H), 3.90 (s, 3H).

Step B 2-(4-methoxy-2-nitrophenyl)acetonitrile

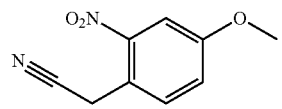

To a stirred solution of 1-(bromomethyl)-4-methoxy-2-nitrobenzene, prepared as described in Step A, (40 g, 0.163 mol) in THF (500 mL) and EtOH (100 mL) was added a solution of KCN (26.6 g, 0.408 mol) in water (100 mL). The reaction mixture was stirred at 0° C. for 1 h and then further for 3 h at room temperature. The reaction mixture was diluted with water (500 mL) and aqueous phase was extracted with DCM (500 mL) and then washed with brine, dried over $Na_2SO_4$ and evaporated in vacuo. The residue was purified by chromatography on a silica gel column to give the title compound. ESI-MS (M+1) 193. $^1$H NMR: ($CDCl_3$, 400 MHz): δ (ppm) 7.72 (s, 1H), 7.63-7.61 (d, 1H), 7.26-7.23 (d, 1H), 4.14 (s, 2H), 3.93 (s, 3H).

Step C ethyl 3-cyano-3-(4-methoxy-2-nitrophenyl)propanoate

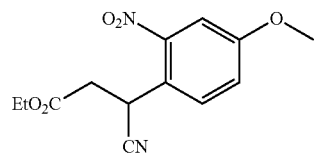 [SMILES: CCOC(=O)CC(C#N)c1ccc(OC)cc1[N+](=O)[O-]]

To a solution of 2-(4-methoxy-2-nitrophenyl)acetonitrile, prepared as described in Step B, (5.5 g, 0.0286 mol) in DMF (100 mL) was added BrCH$_2$CO$_2$Et (5.71 g, 0.034 mol) and K$_2$CO$_3$ (11.86 g, 0.086 mol) at 0° C. The reaction mixture was stirred at 0° C. for 1 h and at room temperature for another 2 h. After the reaction was completed by TLC monitoring, water was added. The reaction was extracted with ethyl acetate; the organic phase was washed with brine, dried over Na$_2$SO$_4$, and concentrated in vacuo. The crude product was purified by chromatography on a silica gel column to give the title compound. ESI-MS (M+1) 279. $^1$H NMR: (CDCl$_3$, 400 MHz): δ (ppm) 7.70-7.68 (d, 1H), 7.57-7.56 (s, 1H), 7.24-7.21 (d, 1H), 5.13-4.98 (m, 1H), 4.20-4.18 (m, 2H), 3.89 (s, 3H), 2.99-2.97 (d, 2H), 1.28-1.24 (t, 3H).

Step D 7-methoxy-2-oxo-1,2,3,4-tetrahydroquinoline-4-carbonitrile

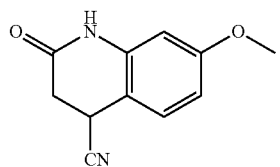

To a solution of ethyl 3-cyano-3-(4-methoxy-2-nitrophenyl)propanoate, prepared as described in Step C, (9.0 g, 0.032 mol) in MeOH (100 mL), Sn (19.3 g, 0.162 mol) was added, followed by hydrochloric acid/MeOH (40 ml, 1:1) all at once. The reaction was stirred at room temperature for 2 h. The solvent was removed in vacuo. Then ethyl acetate was added, and aqueous NaHCO$_3$ solution was added to neutralize the solution. The organic phase was concentrated to get crude product which was used for next step without further purification.

Step E 4-(aminomethyl)-7-methoxy-3,4-dihydroquinolin-2(1H)-one

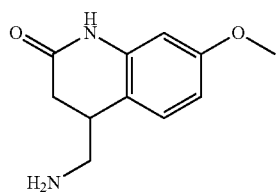

Crude 7-methoxy-2-oxo-1,2,3,4-tetrahydroquinoline-4-carbonitrile, prepared as described in Step D, (6 g, 0.03 mol) and Raney Ni (10 g) was suspended in a mixture of MeOH (100 mL) and 3 mL of triethylamine. The reaction mixture was stirred under H$_2$ (50 Psi) atmosphere at room temperature for 4 h. After the reaction was completed by monitoring by TLC, the catalyst was filtered off, and then the solvent was removed in vacuo to afford the crude product which was used for next step without further purification.

Step F 4-(aminomethyl)-7-hydroxy-3,4-dihydroquinolin-2(1H)-one

To a solution of crude 4-(aminomethyl)-7-methoxy-3,4-dihydroquinolin-2(1H)-one, prepared as described in Step E, (8.8 g, 0.0427 mol) in dichloromethane (100 mL), BBr$_3$ (85 g, 0.342 mol) in dichloromethane (1M) was added dropwise at −14° C., and the reaction was stirred at room temperature overnight. After the reaction was completed by monitoring through TLC, methanol was added slowly at 0° C. to quench the reaction, and the solvent was evaporated in vacuo to get crude product which was used directly in the next step.

Step G tert-butyl ((7-hydroxy-2-oxo-1,2,3,4-tetrahydroquinolin-4-yl)methyl)carbamate

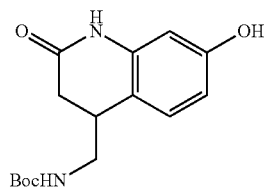

Crude 4-(aminomethyl)-7-hydroxy-3,4-dihydroquinolin-2(1H)-one, prepared as described in Step F, (8.2 g, 0.0427 mol) and (Boc)$_2$O (4.65 g, 0.021 mol), triethylamine (10 mL) were added to 100 mL of methanol. The reaction was stirred at room temperature for 2 h. After the reaction was stopped, the solvent was removed in vacuo, and ethyl acetate was added. The organic phase was washed with water, aqueous NaHCO$_3$ solution, dried over Na$_2$SO$_4$ and concentrated in vacuo. The crude product was purified by chromatography to give the title compound. ESI-MS (M+1) 292. $^1$H NMR: (DMSO-d$_6$, 400 MHz): δ (ppm) 9.96 (s, 1H), 9.31 (s, 1H), 6.95-6.89 (m, 2H), 6.33 (d, 2H), 3.00-2.97 (m, 2H), 2.90-2.96 (m, 1H), 2.56 (m, 1H), 2.30-2.34 (m, 1H), 1.37 (s, 9H).

Step H tert-butyl ((7-(4-bromobutoxy)-2-oxo-1,2,3,4-tetra-hydroquinolin-4-yl)methyl)carbamate

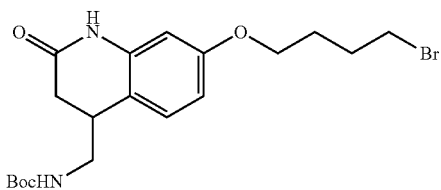 [SMILES: CC(C)(C)OC(=O)NCC1CC(=O)Nc2cc(OCCCCBr)ccc21]

To a solution of tert-butyl ((7-hydroxy-2-oxo-1,2,3,4-tetrahydroquinolin-4-yl)methyl)carbamate, prepared as described in Step H, (1.0 mmol, 292 mg) and 1,4-dibromobutane (1.1 mmol, 237.5 mg) in DMF (1.5 mL) was added anhydrous $K_2CO_3$ (1.2 mmol, 166 mg). The mixture was stirred at room temperature overnight until HPLC and LC/MS indicated that the reaction was complete to give the title compound, which was subjected to next reaction without purification. MS m/z 428 (MH$^+$).

Step I tert-butyl ((7-(4-(4-(2,3-dichlorophenyl)piperazin-1-yl)butoxy)-2-oxo-1,2,3,4-tetrahydroquinolin-4-yl)methyl)carbamate

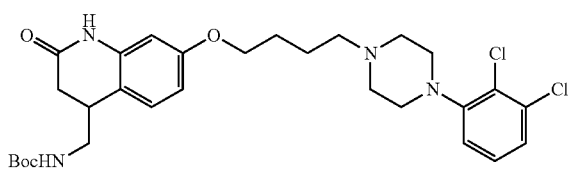 [SMILES: CC(C)(C)OC(=O)NCC1CC(=O)Nc2cc(OCCCCN3CCN(c4cccc(Cl)c4Cl)CC3)ccc21]

To a solution of tert-butyl ((7-(4-bromobutoxy)-2-oxo-1, 2,3,4-tetrahydroquinolin-4-yl)methyl)carbamate, prepared as described in Step H, in DMF was added 1-(2,3-dichlorophenyl)-piperazine hydrochloride (1.0 mmol, 268 mg) and $K_2CO_3$ (1.23 mmol, 170 mg). The mixture was stirred at room temperature overnight. The solvent was evaporated in vacuo and the residue was partitioned between dichloromethane and saturated aqueous $NaHCO_3$ solution. The organic layer was separated and aqueous layer was extracted with additional dichloromethane. Organic layers were combined, concentrated. The residue was then subjected to column chromatography on silica gel with gradient 0-10% methanol in dichloromethane to give the title compound as a solid. MS m/z 578 (MH$^+$).

Step J 4-(aminomethyl)-7-(4-(4-(2,3-dichlorophenyl)piperazin-1-yl)butoxy)-3,4-dihydroquinolin-2(1H)-one

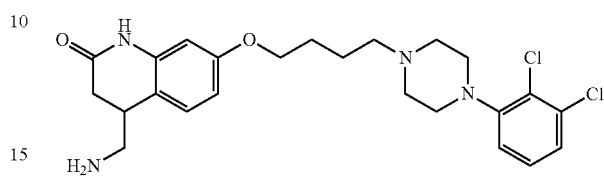

To a solution of tert-butyl ((7-(4-(4-(2,3-dichlorophenyl)piperazin-1-yl)butoxy)-2-oxo-1,2,3,4-tetrahydroquinolin-4-yl)methyl)carbamate, prepared as described in Step I, (200 mg, 0.35 mmol) in dichloromethane (5 mL) was added 1 mL of TFA. The mixture was stirred at room temperature for 2.5 hr. The solvent was evaporated in vacuo and the residue was partitioned between dichloromethane and saturated $NaHCO_3$ solution. The organic layer was separated and aqueous layer was extracted with additional dichloromethane. The organic layers were combined, dried over $Na_2SO_4$, filtered and concentrated. The residue was then subjected to column chromatography on silica gel with 10% methanol in dichloromethane, followed by 10% 7N ammonia methanol in dichloromethane, to give the title compound as a solid. This product was further purified by recrystallization from dichloromethane and heptanes to give final product as a white solid. MS m/z 477 (MH$^+$). $^1$H NMR: (CDCl$_3$, 400 MHz): δ (ppm) 7.40 (s, 1H), 7.25-7.05 (m, 3H), 7.00 (d, 1H), 6.60 (d, 1H), 6.30 (s, 1H), 4.00 (m, 2H), 3.10 (m, 4H), 3.00-2.60 (m, 9H), 2.50 (m, 2H), 1.90-1.40 (m, 6H). Calculated for $C_{24}H_{30}Cl_2N_4O_2$ C, 60.38; H, 6.33; N, 11.74. Found C, 60.32; H, 5.89; N, 11.26.

Example 2

7-(4-(4-(4-amino-2,3-dichlorophenyl)piperazin-1-yl)butoxy)-3,4-dihydroquinolin-2(1H)-one

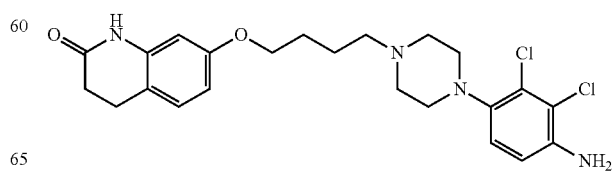

Step A 4-bromo-2,3-dichloro-N-(4-methoxybenzyl)aniline

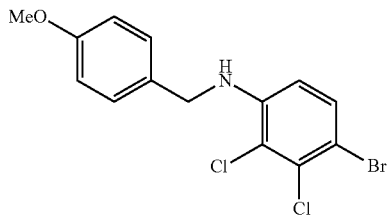 [SMILES: COc1ccc(CNc2ccc(Br)c(Cl)c2Cl)cc1]

To a solution of 4-bromo-2,3-dichloro-phenylamine (3.215 g, 13.3 mmol) and 1-chloromethyl-4-methoxy-benzene (2.297 g, 14.7 mmol) in 23 mL of DMF was added potassium iodide (2.214 g, 13.3 mmol) and 647 mg of sodium hydride (60% oil dispersion). After stirring at room temperature overnight, the reaction mixture was evaporated in vacuo and the residue was partitioned between dichloromethane and saturated NaHCO$_3$ aqueous solution. The organic layer was separated and aqueous layer was extracted with additional dichloromethane. The organic layers were combined, dried over Na$_2$SO$_4$, filtrated, and concentrated. The residue was then subjected to column chromatography on silica gel with 30% ethyl acetate in heptanes to give the title compound as a yellow solid; MS m/z 362 (MH$^+$).

Step B 2,3-dichloro-N-(4-methoxybenzyl)-4-(piperazin-1-yl)aniline

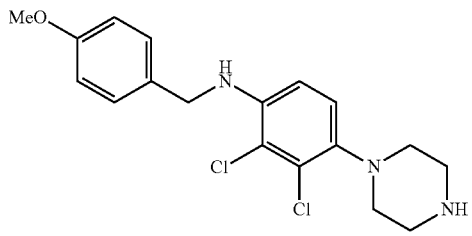 [SMILES: COc1ccc(CNc2ccc(N3CCNCC3)c(Cl)c2Cl)cc1]

A mixture of 4-bromo-2,3-dichloro-N-(4-methoxybenzyl) aniline, prepared as described in the previous step, (3.61 g, 10 mmol), piperizine (1.034 g, 12 mmol), sodium t-butoxide (1.16 g, 12 mmol), and tris(dibenzylideneacetone)dipalladium(0) (180 mg, 2 mol %) in 16 mL of toluene in a sealed thick-wall flask was stirred and heated in an oil bath at 100° C. for 2.5 days. After cooling to room temperature, the reaction mixture was partitioned between dichloromethane and water. The organic layer was separated and aqueous layer was extracted with additional dichloromethane. The organic layers were combined, dried over Na$_2$SO$_4$, filtered, and concentrated. The residue was purified by column chromatography on silica gel column with 10% methanol in dichloromethane, followed by 10% 7N ammonia methanol in dichloromethane, to give the title compound as a light brown solid. MS m/z 367 (MH$^+$). $^1$H NMR: (CDCl$_3$, 400 MHz): δ (ppm) 7.28 (d, 2H), 6.98 (d, 2H), 6.50 (d, 1H), 4.60 (s, 1H), 4.30 (m, 2H), 3.80 (m, 3H), 3.10-2.85 (m, 8H), 2.30 (s, 1H).

Step C 2,3-dichloro-4-(piperazin-1-yl)aniline

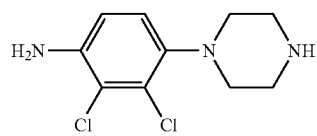

To a solution of 2,3-dichloro-N-(4-methoxybenzyl)-4-(piperazin-1-yl)aniline, prepared as described in the previous step, (562 mg, 1.54 mmol) in dichloromethane (5 mL) was added 5 mL of TFA. The reaction mixture was stirred at room temperature for 5 hr, and then was evaporated in vacuo to dryness. The residue was re-dissolved in dichloromethane and evaporated to dryness. The title compound was used in the next reaction without purification. MS m/z 245 (MH$^+$).

Step D 7-(4-(4-(4-amino-2,3-dichlorophenyl)piperazin-1-yl) butoxy)-3,4-dihydroquinolin-2(1H)-one

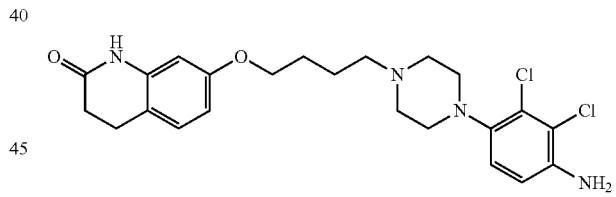

To a solution of 2,3-dichloro-4-(piperazin-1-yl)aniline, prepared as described in the previous step, (1.535 mmol) as TFA salt in DMF (6 mL) was added a solution of commercially available 7-(4-bromo-butoxy)-3,4-dihydro-1H-quinolin-2-one (1.535 mmol) in DMF (1 mL), K$_2$CO$_3$ (2.121 g), and 1 mL of DMF. The resultant mixture was stirred at room temperature overnight. The solid was filtered and rinsed with dichloromethane. The solution was evaporated in vacuo and the residue was then subjected to column chromatography on silica gel with gradient 0-10% methanol in dichloromethane, followed by 10% 7N ammonia methanol in dichloromethane, to give the title compound as a solid. MS m/z 463 (MH$^+$). $^1$H NMR: (DMSO-d$_6$, 400 MHz): δ (ppm) 10.0 (s, 1H), 7.05 (d, 1H), 6.95 (d, 1H), 6.75 (d, 1H), 6.50 (d, 1H), 6.45 (s, 1H), 5.3 (s, 2H), 3.90 (m, 2H), 2.90-2.70 (m, 6H), 2.50-2.30 (m, 8H), 1.80-1.50 (m, 4H). Calculated for C$_{23}$H$_{28}$Cl$_2$N$_4$O$_2$ is C, 59.61; H, 6.09; N, 12.09. Found C, 59.44; H, 5.87; N, 11.77.

Example 3

4-((2,3-dichloro-4-(4-(4-((2-oxo-1,2,3,4-tetrahydro-quinolin-7-yl)oxy)butyl)piperazin-1-yl)phenyl)amino)-4-oxobutanoic acid

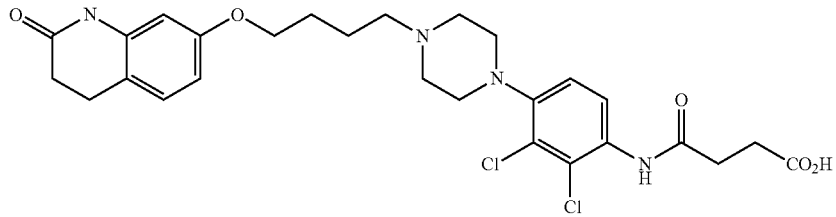 [SMILES: O=C(O)CCC(=O)Nc1ccc(N2CCN(CCCCOc3ccc4c(c3)NC(=O)CC4)CC2)c(Cl)c1Cl]

A solution of Example 2 (115.5 mg, 0.25 mmol) and succinic anhydride (50 mg, 0.5 mmol) in pyridine (1.5 mL) was stirred and heated at 110° C. in a microwave oven for 5.5 hr. The solution was evaporated in vacuo to dryness. The residue was re-dissolved in dichloromethane and evaporated to dryness; and then re-dissolved in methanol and evaporated to dryness. The crude product was purified on a Agela hilic column with gradient 0-20% methanol in dichloromethane to give a solid, which was further purified by recrystallization from methanol and dried at 40-50° C. in a vacuum oven to give the title compound. MS m/z 563 (MH$^+$). $^1$H NMR: (DMSO-d$_6$, 400 MHz): δ (ppm) 12.1 (s, 1H), 10.0 (s, 1H), 9.60 (s, 1H), 7.5 (d, 1H), 7.15 (d, 1H), 7.05 (d, 1H), 6.50 (d, 1H), 6.45 (s, 1H), 3.90 (m, 2H), 3.00 (m, 4H), 2.30 (m, 2H), 2.20-2.30 (m, 12H), 1.80-1.55 (m, 4H). Calculated for $C_{27}H_{33}Cl_2N_4O_5$ is C, 57.55; H, 5.72; N, 9.94. Found C, 55.92; H, 5.85; N, 9.58.

Example 4

5-((2,3-dichloro-4-(4-(4-((2-oxo-1,2,3,4-tetrahydro-quinolin-7-yl)oxy)butyl)piperazin-1-yl)phenyl)amino)-5-oxopentanoic acid

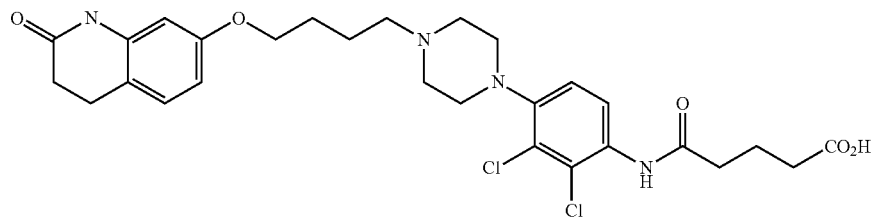 [SMILES: O=C(O)CCCC(=O)Nc1ccc(N2CCN(CCCCOc3ccc4c(c3)NC(=O)CC4)CC2)c(Cl)c1Cl]

A solution of Example 2 (83 mg, 0.18 mmol) and glutaric anhydride (41 mg, 0.36 mmol) in pyridine (1.0 mL) was stirred and heated at 110° C. in a microwave oven for 4.5 hr. The solution was evaporated in vacuo to dryness. The residue was purified on an Agela hilic column (12 g) with gradient 0-30% methanol and dried at 40-50° C. in a vacuum oven to give the title compound. MS m/z 578 (MH$^+$).

Example 5

4-(((7-(4-(4-(2,3-dichlorophenyl)piperazin-1-yl)butoxy)-2-oxo-1,2,3,4-tetrahydroquinolin-4-yl)methyl)amino)-4-oxobutanoic acid

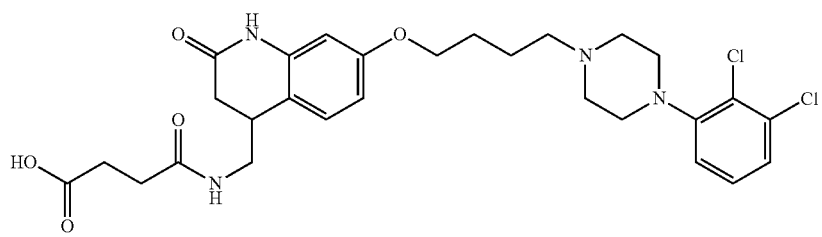 [SMILES: O=C(O)CCC(=O)NCC1CC(=O)Nc2cc(OCCCCN3CCN(c4cccc(Cl)c4Cl)CC3)ccc21]

A solution of Example 1 (24.1 mg, 0.05 mmol) and succinic anhydride (10 mg, 0.10 mmol) in THF (1.0 mL) was stirred at room temperature overnight. The solution was evaporated in vacuo to dryness. The residue was purified on a silica gel column (12 g) with gradient 0-30% methanol in dichloromethane and dried at 40-50° C. in a vacuum oven to give the title compound. MS m/z 578 (MH$^+$).

Example 6

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide

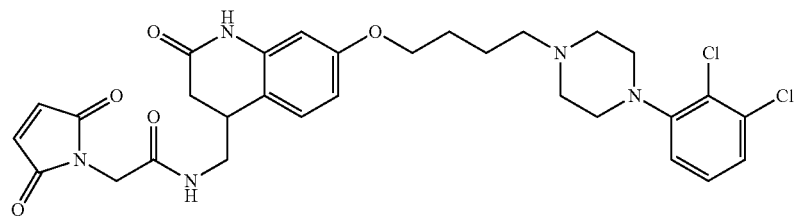 [SMILES: O=C(CN1C(=O)C=CC1=O)NCC1CC(=O)Nc2cc(OCCCCN3CCN(c4cccc(Cl)c4Cl)CC3)ccc21]

To a solution of Example 1 (MW 477.4 2.2 mg, 4.61 µmoles) in 110 µL of DMF and 2.3 µL of tributylamine was added 116 µL of a DMF solution of N-(α-maleimidoacetoxy) succinimide ester (AMAS, MW 252.2, 10 mg/mL, 1.16 mg, 4.61 µmoles). The resulting solution was allowed to stir for 90 minutes at 20° C., and then used as such in conjugation reaction with thiol-activated protein.

Example 7

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide-keyhole limpet hemocyanin conjugate To 3.23 mL of a solution of keyhole limpet hemocyanin (KLH MW 100,000 14.6 mg, 0.146 µmoles) in 100 mM phosphate buffer, 0.46M sodium chloride, pH 7.4 was added 33.7 µL of a DMF solution of N-Succinimidyl-5-acetylthioacetate (SATA MW 231.2, 25 mg/mL, 0.84 mg, 3.65 µmoles). The resulting solution was incubated at 20° C. for 1 hour on a roller mixer. The reaction was purified on a Sephadex G-25 column using 100 mM phosphate buffer, 0.46M sodium chloride, and 5 mM EDTA, at pH 6.0. To 6.46 mL of the KLH-SATA solution (13.7 mg, 0.137 µmoles) was added 646 µL of 2.5M hydroxylamine, and 50 mM EDTA, at pH 7.0. The resulting solution was incubated at 20° C. for 1 hour on a roller mixer. The reaction was treated with 169.6 µL of N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide solution (prepared as described in example 6) (3.43 µmoles). The resulting cloudy mixture was incubated for 2 hours at 20° C. on a roller mixer. The reaction was filtered through a 0.2 µm syringe filter then purified on a Sephadex G-25 column using 100 mM phosphate buffer and 0.46M sodium chloride at pH 7.4, to give the KLH conjugate of Example 6.

Example 8

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide-bovine thyroglobulin conjugate To 2.14 mL of a solution of bovine thyroglobulin (BTG, MW 660,000, 21.8 mg, 0.033 µmoles) in a 100 mM phosphate buffer at pH 7.5 was added 61.1 µL of a DMF solution of N-succinimidyl-5-acetylthioacetate (SATA, MW 231.2, 25 mg/mL, 1.53 mg, 6.6 µmoles). The resulting solution was incubated at 20° C. for 1 hour on a roller mixer. The reaction was purified on a Sephadex G-25 column using 100 mM phosphate buffer, 5 mM EDTA, at pH 6.0. To 5.79 mL of BTG-SATA (20.5 mg, 0.031 µmoles) was added 579 µL of 2.5M hydroxylamine, and 50 mM EDTA, at pH 7.0. The resulting solution was incubated at 20° C. for 1 hour on a roller mixer. The reaction was treated with 304.0 µL of N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide solution (prepared as described in example 6) (6.2 µmoles). The resulting cloudy mixture was incubated for 2 hours at 20° C. on a roller mixer. The reaction was filtered through a 0.45 µm syringe filter then purified on a Sephadex G-25 column using 100 mM phosphate buffer and 0.14M sodium chloride at pH 7.4, to give the bovine thyroglobulin conjugate of Example 6.

Example 9

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide-ovalbumin conjugate Step A To 1.0 mL of a solution of ovalbumin (MW 44,300, 10.0 mg, 0.23 µmoles) in 100 mM phosphate buffer at pH 7.5 was added 31.3 µL of a DMF solution of N-Succinimidyl-S-acetylthioacetate (SATA, MW 231.2, 25 mg/mL, 0.78 mg, 3.4 µmoles). The resulting solution was incubated at 20° C. for 1 hour on a roller mixer. The reaction was treated with 100 µL of 2.5M hydroxylamine and 50 mM EDTA at pH 7.0. The resulting solution was incubated at 20° C. for 15 minutes on a roller mixer. The reaction was purified on a Sephadex G-25 column using 100 mM phosphate buffer and 5 mM EDTA at pH 6.0.

Step B

To the ovalbumin-SH, (30.1 mL, 8.3 mg, 0.187 µmol), prepared as described in Step A, was added N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide solution (prepared as described in example 6) ((185.7 μL, 3.75 μmoles). The resulting cloudy mixture was incubated for 2.5 hours at 20° C. on a roller mixer. The reaction was filtered through a 0.45 μm syringe filter, then purified on a Sephadex G-25 column using 100 mM phosphate buffer, 0.14M sodium chloride at pH 7.4, to give the ovalbumin conjugate of Example 6.

Example 10

Competitive Immunoassay for Aripiprazole

Following a series of immunizations with the immunogens described above in Examples 7-9, mouse tail bleeds were tested for reactivity using an ELISA. Hybridoma supernatants were also tested, and the ELISA data shown in Table 8 below shows reactivity of several hybridomas (fusion partner was NSO cells).

TABLE 8

| Dilution | Plate 1 | | | | |
|---|---|---|---|---|---|
| | 1 | 2 | 3 | 4 | 5 |
| 400 | 3C1 | 3D7 | 5C6 | 5C7 | 5H11 |
| 400 | | | | | |
| 1200 | | | | | |
| 1200 | | | | | |
| 3600 | | | | | |
| 3600 | | | | | |
| 10800 | | | | | |
| 10800 | | | | | |
| | | | | | |
| 400 | 0.8165 | 0.7299 | 0.196 | 3.2953 | 0.0373 |
| 400 | 0.7057 | 0.5671 | 0.1525 | 2.9591 | 0.0371 |
| 1200 | 0.2413 | 0.2186 | 0.0701 | 1.9242 | 0.0348 |
| 1200 | 0.2474 | 0.2278 | 0.0653 | 1.7829 | 0.0336 |
| 3600 | 0.102 | 0.0963 | 0.0472 | 0.739 | 0.0288 |
| 3600 | 0.099 | 0.0954 | 0.051 | 0.7225 | 0.0281 |
| 10800 | 0.0534 | 0.0526 | 0.0381 | 0.2878 | 0.0215 |
| 10800 | 0.0644 | 0.0588 | 0.0411 | 0.2799 | 0.0326 |

Figure 2:
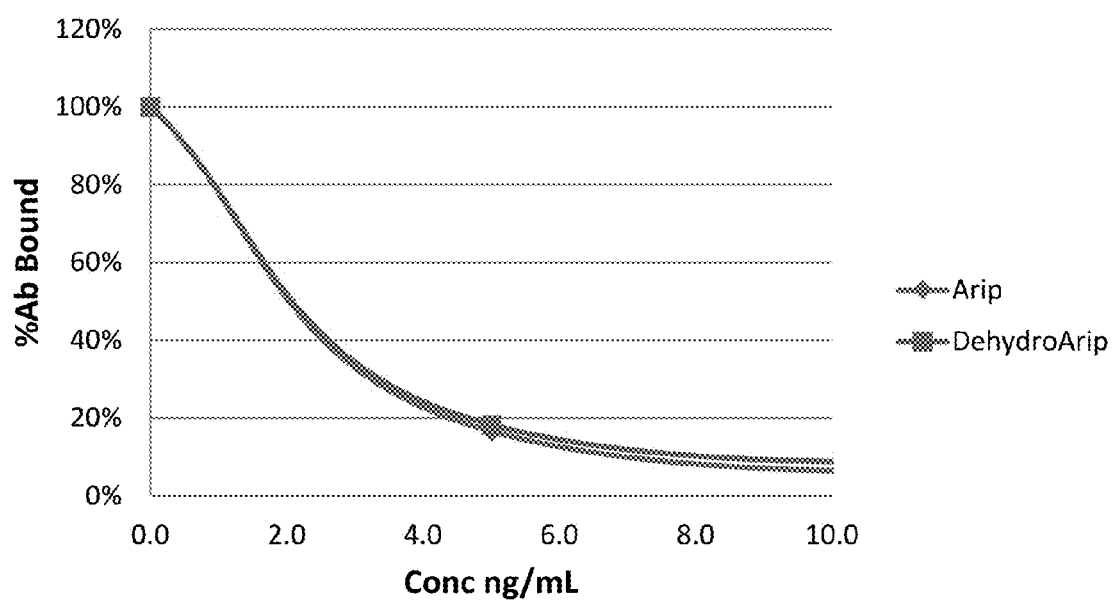
FIG. 2 shows Competition ELISA results generated with hybridoma 3D7.

Supernatant was then tested by competition ELISA to determine if the signal was specific to either aripiprazole or dehydroaripiprazole. FIGS. 1 and 2 show the results from two representative hybridomas, 3C1 and 3D7. Data shows reactivity to both aripiprazole and dehydroaripiprazole.

Figure 3:
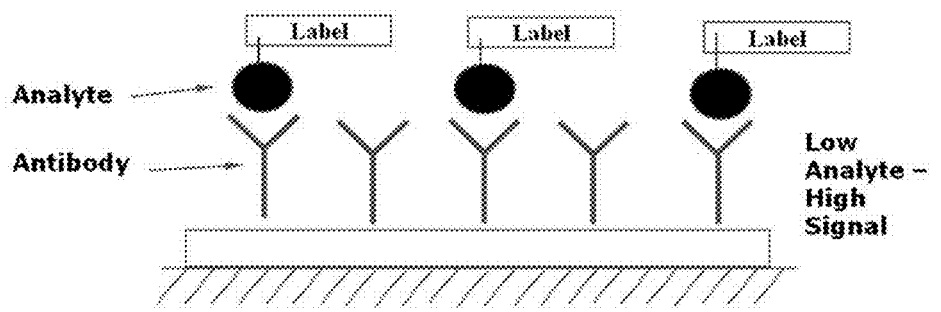
FIG. 3 shows the competitive immunoassay format used on a lateral flow assay device.
Figure 3:
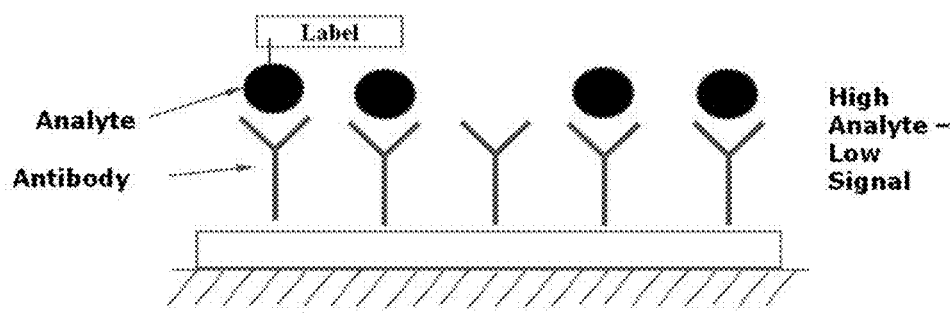
Figure 4:
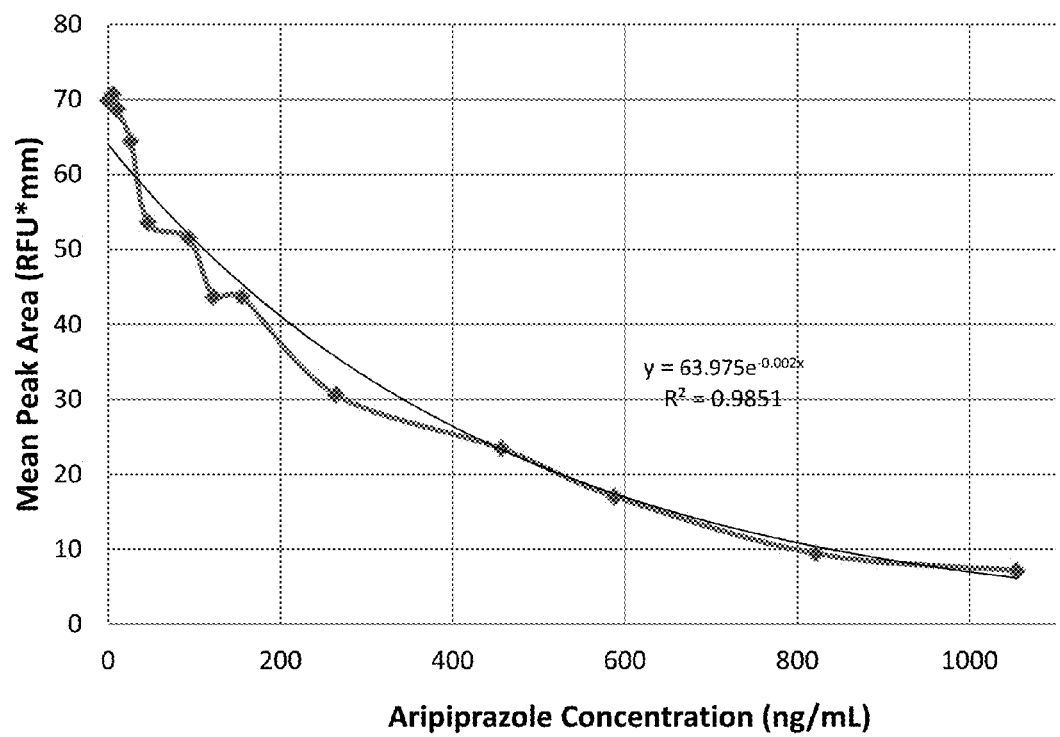
FIGS. 4 and 5 show the results generated with capture antibody aripiprazole clone 5C7 on the lateral flow assay device.
Figure 5:
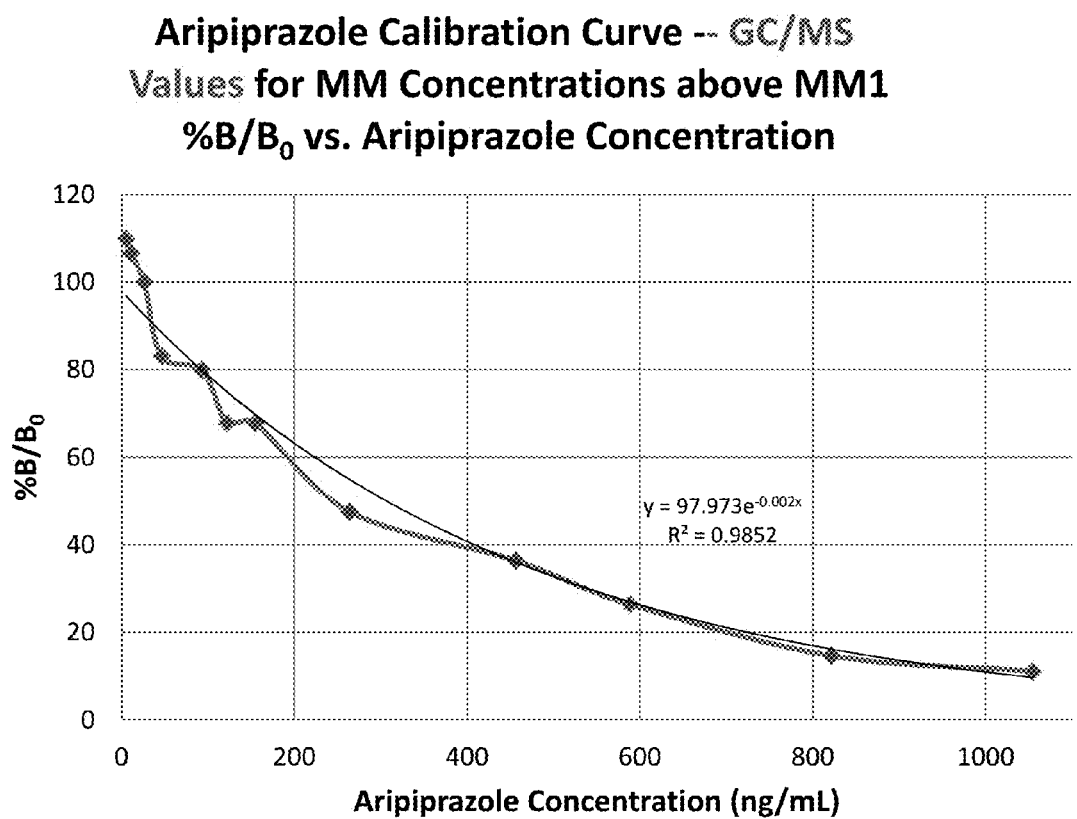

FIG. 3 shows the competitive immunoassay format used on a lateral flow assay device in which the capture antibody, aripiprazole clone 5C7, was deposited on a chip along with a detection conjugate consisting of aripiprazole conjugated to a fluorophore. In this competitive format as show in FIG. 3, a low level of analyte (aripiprazole) results in high signal, whereas a high level of analyte (aripiprazole) results in low signal. Referring to FIGS. 4 and 5 which show the results from the assay as run on a lateral flow assay device, as the dose of aripiprazole in the sample increased, it competed for binding sites on the antibodies. The amount of aripiprazole in the sample can thus be calculated from the loss in fluorescence compared to a sample with no drug present.

All documents cited herein are incorporated by reference. While the foregoing specification teaches the principles of the present invention, with examples provided for the purpose of illustration, it will be understood that the practice of the invention encompasses all of the usual variations, adaptations and/or modifications as come within the scope of the following Claims and their equivalents.

We claim:
1. The compound of Formula I:

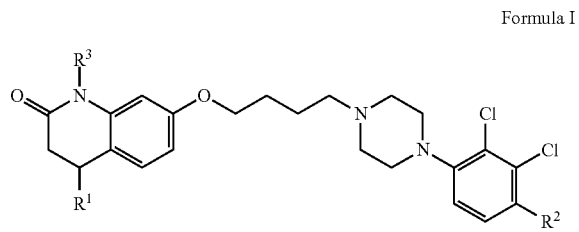

Formula I wherein:
$R^1$ is H,

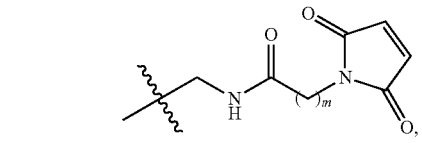

$CH_2NH_2$, or $CH_2NHC(O)(CH_2)_mCO_2H$;
$R^2$ is H,

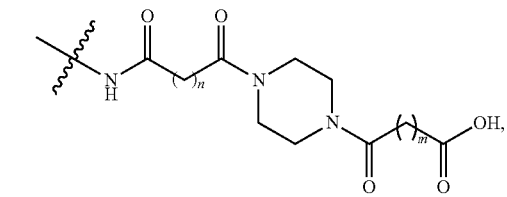

$NH_2$, or $NHC(O)(CH_2)_mCO_2H$;
$R^3$ is H; provided that either $R^1$ or $R^2$ must be H, and further provided that $R^1$ and $R^2$ may not be H simultaneously;
m is 1, 2, 3, 4, or 5; and
n is 1, 2, 3, 4, or 5.

2. The compound of claim 1
wherein:
$R^1$ is H

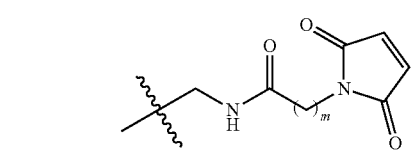

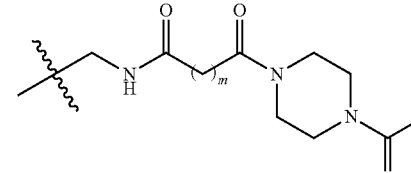

$CH_2NH_2$, or $CH_2NHC(O)(CH_2)_mCO_2H$;

$R^2$ is H,

[structure: ~NH-C(O)-(CH2)n-C(O)-N(piperazine)N-C(O)-(CH2)m-CO2H with ketone]

NH₂, or NHC(O)(CH₂)ₘCO₂H;
provided that either $R^1$ or $R^2$ must be H, and further provided that both $R^1$ and $R^2$ may not be H simultaneously;
$R^3$ is H;
m is 1, 2, 3 or 4; and
n is 1, 2, 3, 4, or 5.

3. The compound of claim 1 wherein:
$R^1$ is H,

[structure: ~NH-C(O)-(CH2)m-N-maleimide]

CH₂NH₂, or CH₂NHC(O)(CH₂)ₘCO₂H;
$R^2$ is H,

[structure: ~NH-C(O)-(CH2)n-C(O)-N(piperazine)N-C(O)-(CH2)m-CO2H]

NH₂, or NHC(O)(CH₂)ₘCO₂H;
$R^3$ is H, provided that either $R^1$ or $R^2$ must be H, and further provided that both $R^1$ and $R^2$ may not be H simultaneously;
m is 1, 2, 3, 4, or 5; and
n is 1, 2, 3, 4, or 5.

4. The compound of claim 1
wherein:
$R^1$ is H

[structure: ~NH-C(O)-(CH2)m-N-maleimide]

[structure: ~CH2-NH-C(O)-(CH2)m-C(O)-N(piperazine)N-C(O)-(CH2)m-CO2H]

CH₂NH₂, CH₂NHC(O)(CH₂)ₘCO₂H;
$R^2$ is H,

[structure: ~NH-C(O)-(CH2)n-C(O)-N(piperazine)N-C(O)-(CH2)m-CO2H]

NH₂, NHC(O)(CH₂)ₘCO₂H;
provided that either $R^1$ or $R^2$ must be H, and further provided that both $R^1$ and $R^2$ may not be H simultaneously;
$R^3$ is H;
m is 1, 2, or 3; and
n is 1, 2, or 3.

5. The compound of claim 2 wherein:
$R^1$ is H, CH₂NH₂, or CH₂NHC(O)(CH₂)ₘCO₂H;
$R^2$ is H, NH₂, or NHC(O)(CH₂)ₙCO₂H; provided that either $R^1$ or $R^2$ must be H, and further provided that both $R^1$ and $R^2$ may not be H simultaneously;
m is 1, 2 or 3; and
n is 1, 2 or 3.

6. The compound of claim 2
wherein:
$R^1$ is H, CH₂NH₂, or CH₂NHC(O)(CH₂)ₘCO₂H;
$R^2$ is H, NH₂, or NHC(O)(CH₂)ₙCO₂H; provided that either $R^1$ or $R^2$ must be H, and further provided that both $R^1$ and $R^2$ may not be H simultaneously;
m is 2; and
n is 2.

7. The compounds of claim 1, selected from the group consisting of:

[structure: aripiprazole-like compound with CH2NH2 substituent, dichlorophenyl piperazine]

-continued
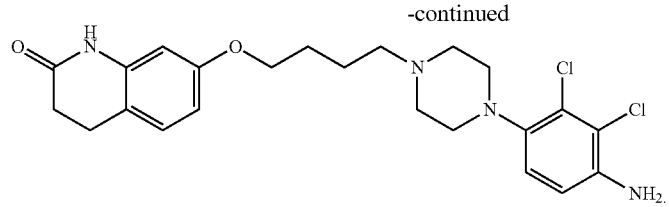
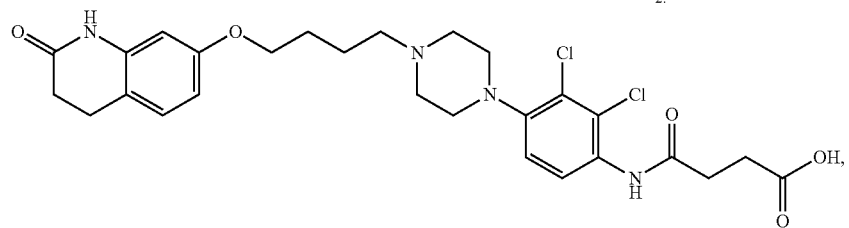
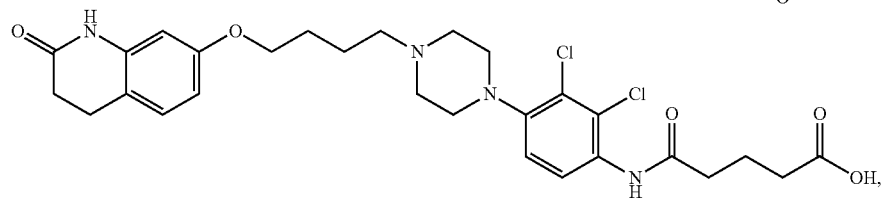
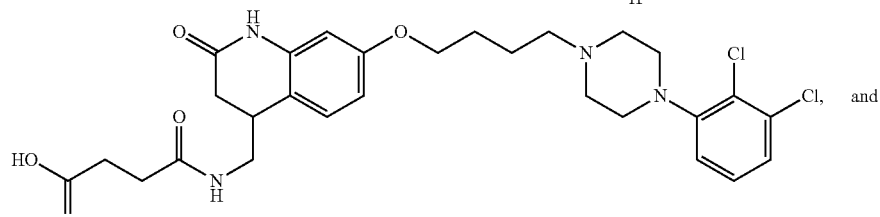
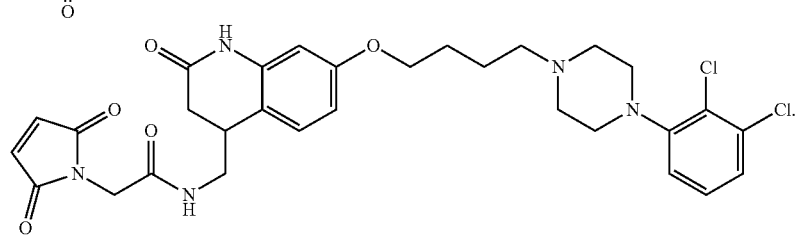
8. The compound of claim 7 which is
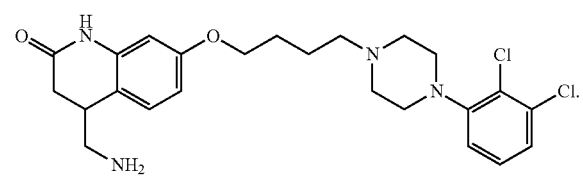 [SMILES: NCC1CC(=O)Nc2cc(OCCCCN3CCN(c4cccc(Cl)c4Cl)CC3)ccc21]
9. The compound of claim 7 which is
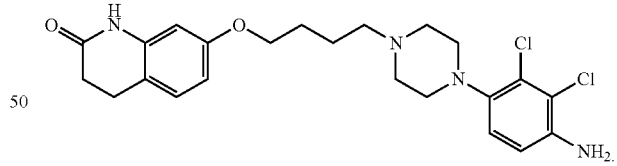
10. The compound of claim 7 which is
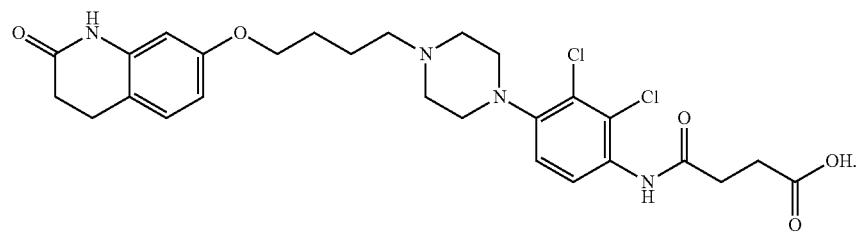 [SMILES: O=C(O)CCC(=O)Nc1ccc(N2CCN(CCCCOc3ccc4c(c3)NC(=O)CC4)CC2)c(Cl)c1Cl]

11. The compound of claim 7 which is
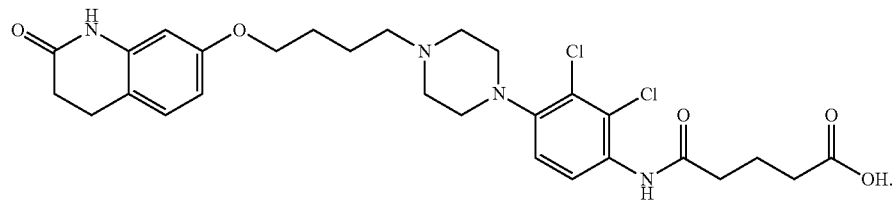 [SMILES: O=C(O)CCCC(=O)Nc1ccc(N2CCN(CCCCOc3ccc4c(c3)NC(=O)CC4)CC2)c(Cl)c1Cl]
12. The compound of claim 7 which is
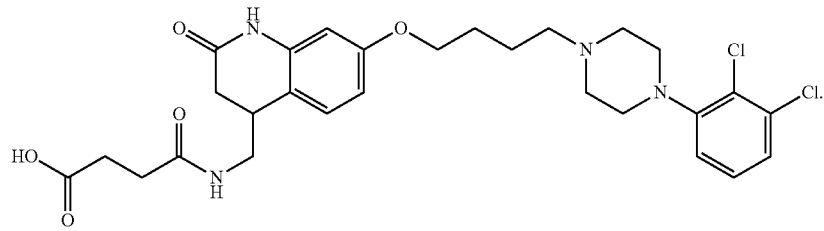 [SMILES: O=C(O)CCC(=O)NCC1CC(=O)Nc2cc(OCCCCN3CCN(c4cccc(Cl)c4Cl)CC3)ccc21]
13. The compound of claim 7 which is
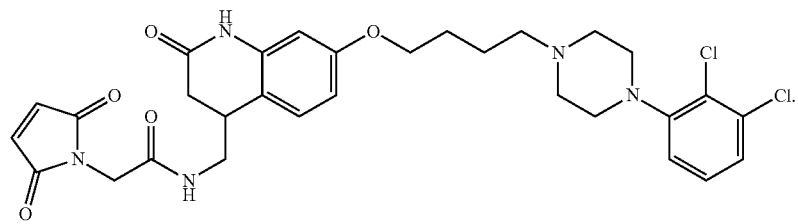 [SMILES: O=C(CN1C(=O)C=CC1=O)NCC1CC(=O)Nc2cc(OCCCCN3CCN(c4cccc(Cl)c4Cl)CC3)ccc21]
* * * * *

UNITED STATES PATENT AND TRADEMARK OFFICE
CERTIFICATE OF CORRECTION

PATENT NO. : 9,504,682 B2  Page 1 of 1
APPLICATION NO. : 13/970650
DATED : November 29, 2016
INVENTOR(S) : Lin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 147 days.

Signed and Sealed this
Twenty-fifth Day of September, 2018

Andrei Iancu
*Director of the United States Patent and Trademark Office*